United States Patent [19]

Hennart et al.

[11] 3,966,900

[45] June 29, 1976

[54] EVAPORATOR SYSTEM COMPRISING A STABILIZED PESTICIDAL PHOSPHORIC ACID ESTER AND METHOD FOR STABILIZING SUCH ESTER ENCLOSED IN AN EVAPORATOR

[75] Inventors: Claude Hennart, Seraincourt; Bernard Rabussier, Aventon; Jean-Pierre Mandon, Poitiers, all of France

[73] Assignee: Airwick Industries, Inc., Carlstadt, N.J.

[22] Filed: Dec. 21, 1973

[21] Appl. No.: 427,103

Related U.S. Application Data

[63] Continuation-in-part of Ser. No. 17,918, March 9, 1970, abandoned.

[30] Foreign Application Priority Data

| Mar. 12, 1969 | France | 69.06860 |
| Mar. 12, 1969 | France | 69.906861 |
| Mar. 12, 1969 | France | 69.06862 |
| Dec. 18, 1969 | Luxemburg | 60052 |

[52] U.S. Cl. ................... 424/27; 260/989; 424/16; 424/219

[51] Int. Cl.$^2$ ............... A01N 17/12; A01N 9/36
[58] Field of Search .................. 424/16, 219, 27

[56] References Cited

UNITED STATES PATENTS

| 3,130,120 | 4/1964 | Schultz et al. | 424/219 |
| 3,470,293 | 9/1969 | Geiger | 424/219 |

FOREIGN PATENTS OR APPLICATIONS

| 280,428 | 12/1965 | Australia | 424/219 |
| 2,096,962 | 3/1972 | France | 424/319 |
| 903,159 | 8/1962 | United Kingdom | 424/219 |

Primary Examiner—Frederick E. Waddell
Attorney, Agent, or Firm—Wenderoth, Lind & Ponack

[57] ABSTRACT

An evaporator system adapted for emitting insect killing vapors of an insecticide therefrom and comprising a liquid or solid composition enclosed therein, said insecticide consisting in at least one volatile phosphoric acid ester which is stabilized by at least one diazene compound.

10 Claims, No Drawings

EVAPORATOR SYSTEM COMPRISING A STABILIZED PESTICIDAL PHOSPHORIC ACID ESTER AND METHOD FOR STABILIZING SUCH ESTER ENCLOSED IN AN EVAPORATOR

The present application is a continuation-in-part of the U.S. Pat. application Ser. No. 17,918 filed on Mar. 9, 1970, now abandoned.

The present invention concerns as novel industrial products new evaporator systems for emitting insect-killing vapors of an insecticide therefrom and comprising a liquid or solid composition enclosed therein and also a new method for the stabilization of volatile phosphoric acid ester pesticides.

Phosphoric acid esters are especially interesting as insecticides and, as such, have experienced a tremendous development during the last years.

One of these is used on a large scale at present in devices called "evaporators" in which advantage is taken of its volatility to obtain an atmosphere which is constantly toxic to insects; this ester is O,O-dimethyl O-(2,2-dichlorovinyl) phosphate, also known under the trade name Dichlorvos or the abbreviation DDVP.

Phosphoric acid esters, and DDVP in particular, have, as is known, the drawback of being susceptible to atmospheric conditions, and, in particular, to humidity and/or light, or to the water introduced into the evaporator system by other constituents thereof, thus causing at least partial decomposition of the esters by protonization, e.g. by replacing a methyl radical by a hydrogen atom.

It has also been found by the Applicants that these phosphoric acid esters, in particular the volatile ones containing one or several lower alkyl radicals, such as, for example the methyl, ethyl, propyl or isopropyl radicals bound to the phosphate anion are susceptible to to the action of an alcoholic compound which more or less rapidly implements the decomposition of said phosphoric acid esters by a protonization reaction such as in the case of hydrolysis. Such volatile phosphoric acid esters are so instable that they undergo a self-protonization reaction even in the absence of humidity. Therefore, it is particularly difficult to stabilize a phosphoric acid ester enclosed in an evaporator which is continually exposed to ambient humidity for long periods of time often exceeding three months.

Various means of stabilization have been proposed to limit the decomposition of the esters in question. Among those used are basic compounds which combine with the phosphoric acid resulting from the decomposition such as amines and lower, nitrogen-containing heterocyclic compounds or antioxydants such as phenolic compounds. These compounds which are usually volatile, are known to possess such a disagreeable odor that they cannot be used in compositions to be employed in inhabited locations, such as evaporators; this is, however, the principal use of phoshoric acid esters. It has also been proposed to use anhydrides or epoxides; it is known that these compounds act by binding either a molecule of water or of acid which has been released; it is recognized that this process is stoichiometrically limited and that as soon as the total amount of the stabilizer has reacted, the stabilization ceases; this requires a large proportion of stabilizer and is thus not very economical. Moreover, such stabilizers do not inhibit the tendency of the molecule to protonize. This is why such stabilizers, although they considerably decrease the decomposition rate of the phosphoric acid esters, are not sufficiently effective to practically entirely suppress decomposition of the insecticidal ester.

It is an object of the present invention to stabilize an evaporator system comprising a volatile phoshoric acid ester pesticide, by employing more effective substances which do not have the drawbacks described above and which effectively prevent the protonization of the molecule of the phosphoric ester.

The term "diazene" designates here two tautomeric forms of organic compounds containing an azo group —N=N—, here called diazenylene, or a hydrazono group —NH—N=, here called diazanylidene. It is known, in fact, that the diazenes known as azo compounds do not necessarily correspond in structure to this name, even if they have been obtained by chemical reaction of diazo coupling and often enough they have a hydrazonic structure (diazanylidene) as has been described by various authors (Hantzsch, Ber., 1899, 32, 3089; Molhau, Ber., 1900, 33, 2858; Tuck, J.Chem.Soc., 1909, 95, 1809; Borsche, Annalen, 1929, 472, 201; Willstatter, Annalen, 1930, 477, 161; Lauer, J.Amer.Chem.Soc., 1935, 57, 520; Kuhn and Baer, Annalen, 1935, 516, 143; Bergmann, Trans. Faraday Soc. 1936, 32, 1318; Sawicki, J.Org.Chem., 1956, 21, 605 and 1957 22, 743; Fischer and Frei, J.Chem.Soc., 1959, p. 3159.)

Furthermore, Applicants have found in the course of experimental work using nuclear magnetic resonance, that the "oxyazo" compounds having a hydrazono-quinonic structure have proved effective.

Thus the instant invention provides an evaporator system adapted for emitting insect-killing vapors of an insecticide therefrom and comprising a liquid or solid composition enclosed therein, which composition contains as the essential constituents:

A. as sole insecticidal active substance from about 8,5 to 99 percent, calculated on the weight of all the ingredients of at least one volatile phosphoric acid ester of the formula:

wherein $R_1$ and $R_2$ are the same or different and represent alkyl radicals containing 1 to 3 carbon atoms, $R_3$ being selected from one of the following groups (i) and (ii):

wherein Y is a halogen atom having an atomic weight of at most 80 and $R_4$ and $R_5$, identical or different, are selected from a hydrogen atom, an aforesaid halogen atom and the methyl, ethyl and propyl radicals, B. as stabilizing agent 0,1 to about 10 percent by weight, based on the weight of (A), of at least one diazene compound of the formula

R — N = N — ZH    (IV)

or of its corresponding tautomeric hydrazonic formula:

R — NH — N = Z    (V)

wherein ZH represents a group

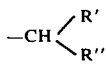

or a group

and Z the corresponding tautomeric divalent groups, R, R', R" and R''' having the following meanings:

R represents a radical of hydroaromatic or aromatic character comprising one, two or three rings, each having 5 or 6 ring members and when said radical contains two or three rings, the rings are condensed together or bound to each other, directly or via an oxygen atom or an —NH—, —CH$_2$—, or

— CH = CH — group and when said radical presents three rings, the latter can form a triphenylmethane group; the radical R being selected from a. carbocyclic radicals of aromatic character having one to three rings and heterocyclic radicals of aromatic character having from one to three rings one of which rings contains one or two ring hetero atoms chosen from nitrogen, oxygen and sulphur;

b. carbocyclic or heterocyclic radicals with hydroaromatic character having two or three carboxylic rings each of 5 or 6 ring members and at least two of these rings are condensed together, wherein two or four carbon atoms in one of the rings are saturated and at least one other ring is aromatic;

c. radicals as defined under (a) or (b) substituted by one or two phenylazo, naphthylazo and/or arylazoarylazo (in which each of the aryl radicals is phenyl or naphthyl) and/or 4-pyrazolyl-azo groups; and d. a radical as defined under (a), (b) or (c) with at least one of its rings bearing one to four substituents selected from fluorine, chlorine, bromine, iodine, keto oxygen, hydroxy, carboxy, alkyl having from one to six carbon atoms, alkylene having from two to five carbon atoms, cycloalkyl having five or six carbon atoms, amino, alkanoylamino having up to five carbon atoms, mono-benzoylamino, alkoxy having from one to five carbon atoms, benzyloxy, nitro, sulpho, cyano, carbamoyl, benzoyl, amino substituted by one or two groups selected from alkyl groups having one to four carbon atoms, phenyl groups and benzyl groups, alkoxycarbonyl having from two to six carbon atoms, alkylsulphonyl having from one to five carbon atoms, sulphamoyl the nitrogen atom of which is unsubstituted or substituted by one or two hydrocarbon radicals having a total of one to eight carbon atoms, alkanoyloxy having at most eighteen carbon atoms, and alkenoyloxy having at most eighteen carbon atoms, alkanoyl having up to five carbon atoms and dialkylamino-alkyl having a total of from three to nine carbon atoms; and R' is benzyl, alkyl of from one to seventeen carbon atoms, alkenyl of two to eight carbon atoms or a radical R as defined under any one of (a) to (d) as defined above and R" is a radical R' as defined above, an unsubstituted phenylazo or naphthylazo group or a phenylazo or naphthylazo group substituted by methyl or ethyl; or R' and R" taken together represent a divalent hydrocarbon radical having a total of four to fourteen carbon atoms which is a straight or branched chain radical or a chain radical containing an aryl ring condensed to the chain, any substitutent of said hydrocarbon radical being selected from the substituents defined under (d), and groups of the formula =NX (in which X represents hydrogen, alkyl having from one to five carbon atoms or phenyl), and the group of formula:

represents a radical R as defined under (a) to (d) above other than a group:

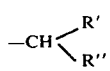

as defined above wherein R' and R" are taken together, or ii. salt of a compound as defined under (i) above being at least one group capable of salt formation, or iii. metal complex of a compound of salt as defined under (i) or (ii) bearing one or two groups, capable of metal complex formation selected from hydroxy, carboxy, amino, mono (C$_1$–C$_4$) alkyl amino, phenylamino, phenylsulphonamino and (C$_1$–C$_4$ alkyl) sulphonamido groups said diazene being dissolved in said composition, and (C) from 0 to about 90%, based on the total weight of the composition of a solid or liquid diluent which is a solvent for components A and/or B.

The instant invention further provides a method for stabilizing a volatile phosphoric acid ester pesticide enclosed in an evaporator system before vapors of said pesticide are emitted into the surrounding atmosphere, said phosphoric acid ester pesticide being selected from at least one compound of the formula (I) defined thereupon said method comprising dissolving in said phosphoric acid ester or in a solution containing said ester, about 0,1 to 10 percent by weight, based on the weight of said ester, of at least one diazene compound of formula (IV) or (V) as defined thereupon.

Preferably, the volatile insecticidal compound A is used in amounts ranging from 3 to 25 percent by weight of the total composition.

Preferably, the evaporator system contains O,O-dimethyl-O(2,2-dichlorovinyl)-phosphate as volatile insecticide. In a preferred embodiment of the evaporator system according to the invention the stabilizing agent is present in an amount from about 0.3 to 5 percent, based on the weight of the phosphoric acid ester. When an insecticidal evaporator system is used in a closed area, insects are killed by breathing the air which is toxic for them, due to the presence of minor amounts of gaseous insecticide, and not by contact-poisoning or ingestion-poisoning as it is the case with all non-volatile insecticides.

As only the volatile phosphoric acid ester and possibly the volatile diluent escape from the evaporator system through evaporation and as the diazene component remains enclosed inside of the evaporator, the latter can act exclusively as a chemical stabilizer for, the still unevaporated liquid insecticide cannot have any biological effect on insects since, due to the very nature of the evaporator system, the composition enclosed in the evaporator can neither be ingested by the insect nor prenetrate into it by contact. Preferably supplementary means are provided for preventing the insecticidal composition from being bodily contacted by the insects. Such means can consist in either a grid, or a diffusion panel, or in a perforated envelope or in any solid diffusing surface from which only gaseous volatile components can evaporate.

The diazenes preferred for practical use according to the invention are chosen from the following clases

—1° MONOAZO COMPOUNDS DEFINED BY THE FOLLOWING FORMULA:

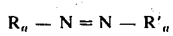

wherein $R_a$ and $R'_a$ are the same or different and each represents phenyl, naphthyl, pyridyl, quinolyl or diphenyl; examples of such compounds are the following:
  azobenzene
  1-phenylazo-naphthalene
  2-phenylazo-naphthalene
  2,2'-azonaphthalene
  1,1'-azonaphthalene
  2,2'-azopyridine
  2,2'-azoquinoline
  o-azodiphenyl
  p-azodiphenyl.

—2° MONO-AZO COMPOUNDS DEFINED BY THE FOLLOWING FORMULA:

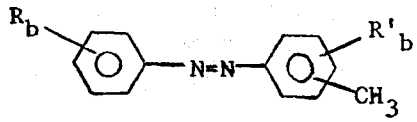

wherein $R_b$ represents hydrogen or one or two methyl radicals, $R'_b$ represents hydrogen or a methyl radical. Examples of such compounds are the following:
  2-methyl-azobenzene
  3-methyl-azobenzene
  4-methyl-azobenzene
  2,2'-dimethyl-azobenzene
  3,3'-dimethyl-azobenzene
  4,4'-dimethyl-azobenzene
  2,2',3,3'-tetramethyl-azobenzene
  3,3',4,4'-tetramethyl-azobenzene
  2,2',4,4'-tetramethyl-azobenzene
  3,3',5,5'-tetramethyl-azobenzene
  2,2',5,5'-tetramethyl-azobenzene.

—3° MONO-AZO COMPOUNDS DEFINED BY THE FOLLOWING FORMULA:

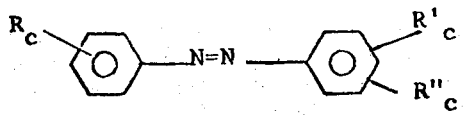

wherein $R_c$ represents hydrogen or one or two halogens, $R'_c$ represents halogen, and $R''_c$ represents hydrogen or halogen, halogen being chlorine, bromine, fluorine or iodine. Examples of such compounds are the following:
  2,2'-dichloro-azobenzene
  3,3'-dichloro-azobenzene
  4,4'-dichloro-azobenzene
  4,4'-difluoro-azobenzene
  2,2'-dibromo-azobenzene
  4,4'-dibromo-azobenzene
  4,4'-diiodo-azobenzene.

—4° MONO-AZO COMPOUNDS DEFINED BY THE FOLLOWING FORMULA:

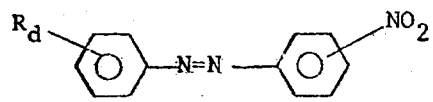

wherein $R_d$ represents hydrogen or a nitro group. Examples of such compounds are the following:
  4-nitro-azobenzene
  3,3'-dinitro-azobenzene
  4,4'-dinitro-azobenzene.

—5° MONO-AZO COMPOUNDS DEFINED BY THE FOLLOWING FORMULA OR BY THE TAUTOMERIC FORMULA OF THE CORRESPONDING IMINOHYDRAZONE COMPOUNDS:

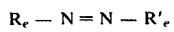

wherein $R_e$ represents a phenyl or naphthyl radical substituted by one or two amino groups which are optionally substituted by an acetyl or benzoyl radical, by one or two phenyl or benzyl radicals or by alkyl having 1 to 4 carbon atoms, the radical $R_e$ being optionally further substituted by one to three substituents chosen from alkyl radicals having 1 to 5 carbon atoms, chlorine, nitro, alkoxy groups having 1 to 3 carbon atoms, alkylsulfonyl groups having 1 to 4 carbon atoms and sulfamoyl groups, the latter being optionally N-substituted by one or two alkyl radicals having 1 to 4 carbon atoms; $R'_e$ represents a phenyl, naphthyl or pyrazolyl radical, optionally substituted by one to three substituents chosen from methoxy, ethoxy and propoxy groups, methyl, ethyl, phenyl and cyclohexyl radicals and chlorine, nitro and amino groups, the latter being optionally substituted by one or two phenyl, benzyl or alkyl radicals having 1 to 4 carbon atoms. Examples of such compounds are the following:
  2-amino-azobenzene
  3-amino-azobenzene
  4-amino-azobenzene
  3,3'-diamino-azobenzene
  4,4'-diamino-azobenzene
  1-phenylazo-4-amino-naphthalene
  1-phenylazo-2-amino-naphthalene
  1-(α-naphthylazo)-4-amino-naphthalene
  1-(α-naphthylazo)-2-amino-naphthalene
  1-(β-naphthylazo)-2-amino-naphthalene
  4-phenylazo-m-phenylene-diamine
  4-phenylazo-diphenylamine 4-(N,N-dimethylamino)-azobenzene
4-(N,N-diethylamino)-azobenzene
1-(2-methyl-phenylazo)-2-amino-naphthalene
4-(α-naphthylazo)-m-phenylene-diamine
4-phenylazo-m-toluylene-diamine
4-amino-4'-nitro-azobenzene
4-(N-benzylamine)-5'-chloro-4'-cyclohexyl-2'-methylazobenzene
1-(2-chloro-4-nitro-phenylazo)-2-amino-5-sulfamoylnaphthalene
1-(2-chloro-4-nitro-phenylazo)-2-amino-5-(N-methylsulfamoyl)-naphthalene
2-(2-chloro-4-nitro-phenylazo)-5-diethylamino-toluene
4-(4-nitro-phenylazo)-3-acetylamino-aniline
4-(4-nitro-phenylazo)-3-methyl-aniline
4-phenylazo-N-acetylaniline
1-(6-chloro-2,4-dinitro-phenylazo)-4-diethylaminonaphthalene
5-(2,4-dinitro-phenylazo)-4-acetylamino-2-(N-benzyl-N-ethyl-amino)-anisole
4-(2,4-dinitro-phenylazo)-5-amino-3-methyl-1-phenylpyrazole
4-(4-ethylsulfonyl-2-nitro-phenylazo)-5-amino-3-methyl-1-phenyl-pyrazole
1-(2-methoxy-4-nitro-phenylazo)-4-diethylamino-toluene.

—6° MONO-AZO COMPOUNDS, KNOWN AS OXYAZO COMPOUNDS DEFINED BY THE FOLLOWING FORMULA OR BY THE TAUTOMERIC FORMULA OF THE CORRESPONDING HYDRAZONOQUINONE COMPOUNDS:

$R_f - N = N - R'_f$ wherein $R_f$ represents a phenyl, naphthyl or quinolyl radical having one or two hydroxy groups and optionally substituted by one to three further substituents chosen from chlorine, alkyl radicals containing 1 to 5 carbon atoms, the cyclohexyl radical, and carbamoyl, carboxy and nitro groups; $R'_f$ represents a phenyl, naphthyl or pyridyl radical optionally further substituted by one to four substituents chosen from chlorine, the cyclohexyl radical, the methyl radical and the hydroxy, nitro, methoxy, benzyloxy, dimethylamino and dimethylaminomethyl groups. Examples of such compounds are the following:

4-hydroxy-azobenzene
2-hydroxy-azobenzene
2,2'-dihydroxy-azobenzene
3,3'-dihydroxy-azobenzene
4,4'-dihydroxy-azobenzene
3,4-dihydroxy-azobenzene
2,6-dihydroxy-azobenzene
2,5-dihydroxy-azobenzene
1-phenylazo-2-naphthol
4-phenylazo-1-naphthol
2-phenylazo-1-naphthol
2-(α-naphthylazo)-1-naphthol
1-(α-naphthylazo)-2-naphthol
1-(β-naphthylazo)-2-naphthol
1-(2-pyridyl-azo)-2-naphthol
4-(4-nitro-phenylazo-resorcinol
4-(4-nitro-phenylazo)-5-methyl-resorcinol
5-(4-nitro-phenylazo)-salicylic acid
4-phenylazo-m-cresol
4-phenylazo-resorcinol
4-phenylazo-o-cresol
1-xylylazo-2-naphthol
1-(o-anisylazo)-2-naphthol
1-(p-anisylazo)-2-naphthol
1-(4-chloro-o-anisylazo)-2-naphthol
3-phenylazo-2,4-dihydroxy-quinoline
3-phenyl-2-hydroxy-quinoline
2,2',4-trihydroxy-5'-nitro-azobenzene
4-(N,N-dimethylamino-2-methyl-phenylazo)-resorcinol
2-(2-benzyloxy-5-chloro-phenylazo)-3,6-disulfo-8-tolylsulfamido-1-naphthol
1-xylylazo-2-naphthol
1-(2-hydroxy-4-nitro-phenylazo)-2-naphthol
1-(2-hydroxy-5-sulfamoyl-phenylazo)-2-naphthol
1-(2-hydroxy-5-nitro-phenylazo)-2-naphthol
2-(4-cyclohexyl-2-methyl-phenylazo)-4-cyclohexylphenol
2-(4-cyclohexyl-2,5-dimethyl-phenylazo)-4-cyclohexylphenol
2-(4-cyclohexyl-2-methoxy-phenylazo)-4-cyclohexyl-phenol
2-(4-cyclohexyl-2-methyl-phenylazo)-5,6,7,8-tetrahydro-2-naphthol
(2,4-dichloro-phenylazo)-2-naphthol.

—7° MONO-AZO COMPOUNDS DEFINED BY THE FOLLOWING FORMULA:

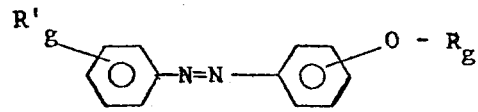

wherein $R_g$ represents an alkyl radical containing 1 to 4 carbon atoms or an alkanoyl radical containing 2 to 18 carbon atoms, $R'_g$ represents hydrogen or an alkoxy group containing 1 to 4 carbon atoms. Examples of such compounds are the following:

4,4'-azoanisole
4,4'-azophenetol
4-methoxy-azobenzene
4-ethoxy-azobenzene
2-acetoxy-azobenzene
2,2'-azophenetol
2,2'-azoanisole
4-butyroxy-azobenzene
4-heptanoyloxy-azobenzene
1-(4-ethoxy-phenylazo)-4-heptanoyloxy-benzene
4-palmitoyloxy-azobenzene
4-lauroyloxy-azobenzene.
4-palmitoyloxy-azobenzene

—8° PHENYLHYDRAZONE COMPOUNDS DEFINED BY THE FOLLOWING FORMULA:

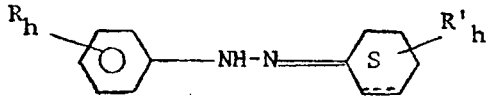

wherein $R_h$ represents hydrogen or one or two substituents chosen from chlorine and the nitro group; $R'_h$ represents hydrogen or one to three alkyl radicals having 1 to 4 carbon atoms; the dotted line represents an optional second bond. Examples of such compounds are the following:
  phenylhydrazonocyclohexane
  4-chloro-phenylhydrazonocyclohexane
  4-nitro-phenylhydrazonocyclohexane
  1-phenylhydrazono-2-methyl-cyclohexane
  1-phenylhydrazono-4-methyl-cyclohexane
  1-phenylhydrazono-3,3,5-trimethyl-cyclohexane
  1-phenylhydrazono-3,5,5-trimethyl-cyclohex-2-ene
  2-phenylhydrazono-methane.

–9° PHENYLHYDRAZONE COMPOUNDS DEFINED BY THE FOLLOWING FORMULA OR BY THE TAUTOMERIC FORMULA OF THE CORRESPONDING HYDROXYAZO COMPOUNDS:

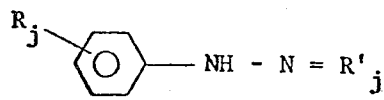

wherein $R_j$ represents one to three substituents chosen from alkyl radicals having 1 to 5 carbon atoms, chlorine, nitro, hydroxy, carboxy, sulfo and methylsulfonyl groups; $R'_j$ represents a 2-indolinon-3-ylidene or a 3,4-dihydro-3-pyrazolon-4-ylidene radical, optionally substituted by a methyl radical and/or a phenyl, chlorophenyl or sulfophenyl radical. Examples of such compounds are the following:
  3-phenylhydrazono-2-indolone
  4-nitro-3-phenylhydrazono-2-indolone
  3-(4-chloro-phenylhydrazono)-2-indolone
  4-phenylhydrazono-1-phenyl-3-methyl-4,5-dihydro-5-pyrazolone
  4-(2-chloro-phenylhydrazono)-1-phenyl-3-methyl-4,5-dihydro-5-pyrazolone
  4-phenylhydrazone-1-(4-sulfo-phenyl)-3-methyl-4,5-dihydro-5-pyrazolone
  4-(2-chloro-phenylhydrazono)-1-(2-chloro-phenyl)-3-methyl-4,5-dihydro-5-pyrazolone
  4-(2-sulfo-phenylhydrazono)-1-(2-chloro-phenyl)-3-methyl-4,5-dihydro-5-pyrazolone
  4-(2-carboxy-phenylhydrazono)-1-phenyl-3-methyl-4,5-dihydro-5-pyrazolone
  4-(2-hydroxy-4-nitro-5-methylsulfonyl-phenylhydrazono)-3-methyl-4,5-dihydro-1-phenyl-5-pyrazolone
  4-(2-hydroxy-3-nitro-5-tert-amyl-phenylhydrazono)-3-methyl-1-phenyl-4,5-dihydro-5-pyrazolone
  4-(2-hydroxy-4-nitro-phenylhydrazono)-3-methyl-1-phenyl-4,5-dihydro-5-pyrazolone.

–10° SYMMETRIC COMPOUNDS KNOWN AS DISAZO COMPOUNDS DEFINED BY THE FOLLOWING FORMULA OR BY THE TAUTOMERIC FORMULA OF THE CORRESPONDING HYDRAZONOQUINONE OR IMINOHYDRAZONE COMPOUNDS WHEN THE DISAZO COMPOUND IS DESCRIBED AS HAVING HYDROXY OR AMINO GROUPS:

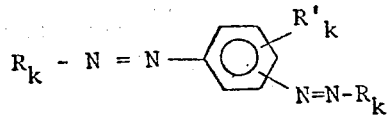

wherein $R_k$ represents a phenyl radical optionally substituted by an amino group or one or two hydroxy and/or methyl radicals; $R'_k$ represents hydrogen or a methyl radical. Examples of such compounds are the following:
  1,4-bis-(phenylazo)-benzene
  1,4-bis-(p-tolylazo)-benzene
  1,3-bis-(4-hydroxy-phenylazo)-benzene
  1,4-bis-(4-hydroxy-phenylazo)-benzene
  1,3-bis-(4-amino-phenylazo)-benzene.

–11° SYMMETRIC COMPOUNDS KNOWN AS DISAZO COMPOUNDS DEFINED BY THE FOLLOWING FORMULA OR BY THE TAUTOMERIC FORMULA OF THE CORRESPONDING HYDROAZONQUINONE OR IMINOHYDRAZONE COMPOUNDS:

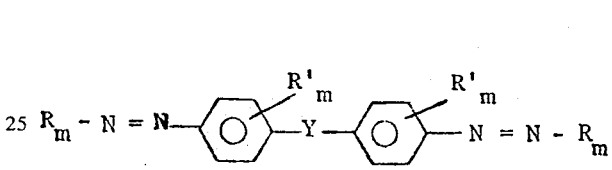

wherein Y represents a direct bond or an oxygen atom or a —CH=CH- or —CH$_2$— group or a —CHR''$_m$— group in which R''$_m$ is a phenyl or chlorophenyl radical; $R_m$ represents a phenyl, naphthyl or 5-pyrazolon-4-yl radical, which radical is optionally substituted by one or two substituents chosen from methyl, phenyl, hydroxy, amino, sulfo and carboxy groups; $R'_m$ represents one or two hydrogen atoms or one or two methyl radicals. Examples of such compounds are the following:
  4,4'-bis-(4-hydroxy-phenylazo)-2,2'-disulfo-stilbene
  4,4'-bis-(4-hydroxy-phenylazo)-diphenyloxide
  4,4''-bis(2,4-diamino-phenylazo)-diphenyloxide
  4,4'-bis-(1-amino-4-sulfo-β-naphthylazo)-biphenyl
  4,4'-bis-(3-carboxy-4-hydroxy-phenylazo)-biphenyl
  4,4'-bis-(4-hydroxy- phenylazo) -diphenylmethane
  4,4'-bis-(4-hydroxy-3-methyl-phenylazo)-diphenylmethane
  4,4'-bis-(4-hydroxy-phenylazo)-triphenylmethane
  4,4'-bis-(4-hydroxy-3-methyl-phenylazo)-triphenylmethane
  α,α-bis-[4-(4-hydroxy-phenylazo)-xylyl]-toluene
  α,α-bis-[4-(4-hydroxy-3-methyl-phenylazo)-xylyl]-toluene
  α,α-bis-[4-(4-hydroxy-phenylazo)-xylyl]-4-chlorotoluene
  4,4'-bis-(2-hydroxy-α-naphthylazo)-diphenylmethane
  4,4'-bis-(2-hydroxy-α-naphthylazo)-triphenylmethane
  α,α-bis-[4-(2-hydroxy-α-naphthylazo)-xylyl]-toluene
  α,α,-bis-[4-(2-hydroxy-α-naphthylazo)-xylyl]-4-chlorotoluene
  4,4'-bis-[(5-methyl-2-phenyl-3-pyrazolol-4-yl)-azo]3,3'-dimethyl-triphenylmethane.

—12° ASYMMETRIC COMPOUNDS KNOWN AS DISAZO COMPOUNDS DEFINED BY THE FOLLOWING FORMULA OR BY THE TAUTOMERIC FORMULA OF THE CORRESPONDING HYDRAZONOQUINONE OR IMINOHYDRAZONE COMPOUNDS WHEN THE DISAZO COMPOUND IS DESCRIBED AS HAVING AT LEAST ONE HYDROXY OR AMINO GROUP:

$$R_n - N = N - R'_n - N = N - R''_n$$

wherein $R_n$ represents a phenyl, diphenyl or naphthyl radical optionally substituted by one of two substituents chosen from the methyl radical and the hydroxy, carboxy and sulfo groups; $R'_n$ represents a divalent, phenylene or naphthylene radical, optionally substituted by one to three substituents chosen from the methyl radical and the amino, hydroxy, nitro and sulfo groups; $R''_n$ represents a phenyl, naphthyl, tetrahydronaphthyl or dihydro-perimidinyl radical, optionally substituted by one to four substituents chosen from the methyl radical and the hydroxy, sulfo, carboxy and amino groups, the latter may be substituted by a methyl or ethyl radical and/or a sulfamoyl group optionally N-substituted by one or two alkyl radicals having 1 to 4 carbon atoms. Examples of such compounds are the following:

1-(4-phenylazo-phenylazo)-2-naphthol
1-(4-o-tolylazo-2-methyl-phenylazo)-2-naphthol
1-(4-phenylazo-phenylazo)-2-ethylamino-naphthalene
1-(1-phenylazo-4-naphthyl-azo)-2-ethylamino-naphthalene
6-(1-phenylazo-4-naphthyl-azo)-2,3-dihydro-2,2-dimethylperimidine
2-(4-phenylazo-phenylazo)-4-sulfo-1-naphthol
1-[4-(4-sulfo-phenylazo)-phenylazo]-2-naphthol
2-phenylazo-7-(4-nitro-phenylazo)-8-amino-3,6-disulfo-1-naphthol
1-[4-(4-sulfo-phenylazo)-2-sulfo-phenylazo]-2-naphthol
4-(3-carboxy-4-hydroxy-phenylazo)-4'-(7-amino-1-hydroxy-3-sulfo-β-naphthylazo)-biphenyl
8-(3-carboxy-4-hydroxy-phenylazo)-4'-(7-amino-1-hydroxy-3-sulfo-β-naphthylazo)-biphenyl
1-(4-phenylazo-phenylazo)-4-ethylamino-naphthalene
1-(4-phenylazo-phenylazo)-5,6,7,8-tetrahydro-2-naphthol
1-(2-xylyl-azo-2,4-xylyl-azo)-2-naphthol
1-(4-xylyl-azo-2,4-xylyl-azo)-5,6,7,8-tetrahydro-2-naphthol
1-(4-α-naphthylazo-α-naphthyl-azo)-5,6,7,8-tetrahydro-2naphthol
1-(4-α-naphthylazo-α-naphthylazo)-2-naphthol
1-(4-phenylazo-phenylazo)-2-hydroxy-6-sulfamoyl-naphthalene
1-(4-phenylazo-phenylazo)-2-hydroxy-6-(N-ethylsulfamoyl)-naphthalene
1-(4-phenylazo-phenylazo)-6-(N-ethylsulfamoyl)-naphthalene
1-(1-phenylazo-4-naphthyl-azo)-2-naphthol.

—13° COMPOUNDS KNOWN AS TRISAZO OR TETRA-AZO COMPOUNDS DEFINED BY THE FOLLOWING FORMULA OR BY THE TAUTOMERIC FORMULA OF THE CORRESPONDING HYDRAZONOQUINONE OR IMINOHYDRAZONE COMPOUNDS WHEN THE COMPOUND IS DESCRIBED AS HAVING AT LEAST ONE HYDROXY OR AMINO GROUP:

$$R_o - N = N - R'_o - N = N - R''_o - N = N - R'''_o$$

wherein $R_o$ represents a phenyl or naphthyl radical, optionally substituted by one to four substituents chosen from hydroxy, carboxy, amino, sulfo and phenylazo or naphthylazo groups, the latter two groups being optionally substituted by one or two substituents chosen from hydroxy, amino, sulfo and nitro groups; $R'_o$ represents a divalent, non-substituted phenylene or diphenylene radical; $R''_o$ represents a divalent phenylene or naphthylene radical, which is non-substituted or substituted by one to four substituents chosen from amino, hydroxy and sulfo groups; $R'''_o$ represents a phenyl or naphthyl radical optionally substituted by one or two substituents chosen from amino, hydroxy and/or sulfo groups. Examples of such compounds are the following:

1-(4-hydroxy-phenylazo)-4-[7-(phenylazo)-8-amino-3,6-disulfo-1-hydroxy-β-naphthylazo]-benzene
4-(3-carboxy-4-hydroxy-phenylazo)-4'-[3-(4-sulfo-phenylazo)-2,6-diamino-phenylazo]-biphenyl
4-(4-hydroxy-phenylazo)-4'-[7-(4-nitro-phenylazo)-8-amino-3,6-disulfo-1-hydroxy-β-naphthylazo]-biphenyl
4--(3,4-diamino-phenylazo)-4'-(2-phenylazo-1-amino-3,6-disulfo-8-hydroxy-β-naphthylazo)-biphenyl
4-[8-(2-hydroxy-α-naphthylazo)-1-hydroxy-3,6-disulfo-β-naphthylazo]-4'-[7-(2-hydroxy-α-naphthylazo)-1-hydroxy-3-sulfo-β-naphthylazo]-biphenyl
4-[8-(2,4-diamino-phenylazo)-1-hydroxy-3,6-disulfo-β-naphthylazo]-4'-[7-(2,4-diamino-phenylazo)-1-hydroxy-3-sulfo-β-naphthylazo]-biphenyl.

—14° FORMAZYL COMPOUNDS DEFINED BY THE FOLLOWING FORMULA:

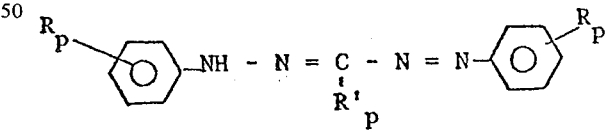

wherein $R_P$ represents hydrogen or a methyl or ethyl radical; $R'_p$ represents a phenyl or benzyl radical or an alkyl radical having 1 to 3 carbon atoms or an alkenyl radical having 2 to 4 carbon atoms. Examples of such compounds are the following:

methylformazyl
ethylformazyl
allylformazyl
4,4'-dimethyl-methylformazyl
4,4'-dimethyl-ethylformazyl
phenylformazyl
benzylformazyl
4,4'-dimethyl-phenylformazyl.

The diazenes employed in the compositions according to the instant invention may also be in the form of their basic and acid salts when such formation is possible.

The diazenes may also be in the form of metal complexes with, for example, chromium, nickel, iron, copper and cobalt; examples of such complexes are the following:

(1:2) chromium complex of 4-(2-hydroxy-4-nitro-5-methylsulfonyl-phenylazo)-3-methyl-1-phenyl-5-pyrazolone (1:2) chromium complex of 4-(2-hydroxy-3-nitro-5-tertamyl-phenylazo)-3-methyl-1-phenyl-5-pyrazolone (1:2) chromium complex of 4-(2-hydroxy-4-nitrophenylazo)-3-methyl-1-phenyl-5-pyrazolone (1:2) cobalt complex of diazo-(2-amino-4-ethylsulfonylphenol) 2-naphthol (1:2) cobalt complex of diazo-(2-amino-4-ethylsulfonylphenol) 2-(N-methoxycarbonyl-N-methyl-amino)-7-naphthol (1:2) chromium complex of 4-(2-hydroxy-5-nitrophenylazo)-resorcinol (1:2) cobalt complex of 4-(2-hydroxy-5-nitrophenylazo)-resorcinol (1:2) chromium complex of 1-(2-hydroxy-5-nitrophenylazo)-2-naphthol (1:2) chromium complex of 4-(5-chloro-2-hydroxyphenylazo)-resorcinol (1:2) chromium complex of 1-(2-hydroxy-4-nitrophenylazo)-2-naphthol (1:2) chromium complex of 4-(2-hydroxy-4-nitrophenylazo)-resorcinol (1:2) chromium complex of 1-(2-hydroxy-3-nitro-5-tertamyl-phenylazo)-2-naphthol (1:2) cobalt complex of 4-(5-chloro-2-hydroxyphenylazo)-resorcinol (1:2) cobalt complex of 4-(2-hydroxy-4-nitrophenylazo)resorcinol (1:2) chromium complex of diazo-(2-amino-5-nitro-4-ethylsulfonyl-phenol) → 8-hydroxy-quinoline (1:2) cobalt complex of diazo-(5-chloro-2-aminophenol) 3-anilinocarbonyl-2-naphthol (1:2) chromium complex of 1-(2-hydroxy-5-nitrophenylazo)-2-naphthol (1:2) nickel complex of 1-(2-hydroxy-5nitrophenylazo)-2-naphthol (1:2) iron complex of 1-(2-hydroxy-5-nitrophenylazo)-2-naphthol (1:2) copper complex of 1-(4,6-dichloro-2-hydroxyphenylazo)-2-naphthol (1:2) chromium complex of 4-(2-hydroxy-5-nitrophenylazo)-3-methyl-1-phenyl-5-pyrazolone (1:2) cobalt complex of 1-(4,6-dichloro-2-hydroxyphenylazo)-2-naphthol (1:2) chromium complex of 4-(2-carboxyphenylazo)-3-methyl-5-pyrazolone (1:2) cobalt complex of 1-(2-hydroxy-5-sulfamoylphenylazo)-2-naphthol.

The use of two or several diazenes instead of only one diazene as stabilizing agent B permits to obtain a better stabilization of the phosphoric ester because mixtures of diazenes show synergistic stabilizing properties. The evaporator system according to the present invention can optionally contain a solid or liquid diluent (C) which is a solvent for the insecticidal active substance and/or for the diazene. This diluent can consist of liquid or solid, volatile or non-volatile pure substances or of mixtures selected from:

a. aliphatic or cycloaliphatic hydrocarbons having a vapor pressure at 20°C up to 30 Torr, preferably up to 5 Torr;

components (C) which are liquid and volatile correspond preferably to products distilling, at atmospheric pressure, between 100° and 320°C, preferably between 140° and 270°C, and which have a vapour pressure above 0.001 Torr. Among the hydrocarbon liquids which can be used as a diluent (C), one can give the following examples:

|  | Distillation (Point°C) | Vapor pressure at 20°C (TORR) | |
|---|---|---|---|
| - n-nonane | 151°C | 3.5 | TORRS |
| - n-decane | 174°C | 1.3 | — |
| - n-undecane | 197°C | 0.45 | — |
| - n-dodecane | 216°C | 0.15 | — |
| - n-tridecane | 234°C | 0.08 | — |
| - n-tetradecane | 252°C | 0.02 | — |
| - 2,6-dimethyl-octane | 159°C | 2.5 | — |
| - white spirit | 150/205°C | 0.2/3.5 | TORRS |
| - "Isopar L" (a) | 189/205°C | 0.2/0.6 | — |
| - "Soltrol 130" (b) | 176/208°C | 0.2/1.2 | — |
| - "Soltrol 160" (b) | 189/205°C | 0.2/0.6 | — |
| - "Aliphatic Solvent 55" (c) | 169/195°C | 0.5/1.6 | TORRS |
| - illuminating oil | 160/230°C | 0.1/2.6 | — |
| - kerosene | 190/235°C | 0.08/0.6 | — |
| - o-menthane | 171°C | 2.0 | TORRS |
| - m-menthane | 158°C | 2.0 | — |
| - p-menthane | 169°C | 2.0 | — |
| - decalin | 187/195°C | 0.9/3 | TORRS |
| - 3,3,4,4-tetramethyl-hexane | 170°C | 1.5 | — |
| - isoamylcyclohexane | 193°C | 1.0 | — |
| - "Solpar 195/230" (d) | 194/225°C | 0.1/0.5 | TORRS |
| - "Solnap" (e) | 150/195°C | 0.5/3.5 | — |
| - "Solvent 30" (f) | 160/200°C | 0.1/2.5 | — |
| - Amsco Solvent 140 (g) | 186/206°C | 0.2/1.0 | — |
| - Apco Solvent 140 (h) | 181/202°C | 0.3/1.1 | — |
| - Odorless Atlantic Solvent (j) | 179/201°C | 0.3/1.2 | — |

4-ethylsulfonyl-phenol) → 2-(2-carboxy-phenyl)-naphthylamine (1:2) cobalt complex of 1-(2-hydroxy-4-nitrophenylazo)-2-amino-naphthalene a. mixture of synthetic branched aliphatic hydrocarbons, constituted by a mixture of decanes, undecanes and dodecanes, produced by the French Company ESSO Standard of Paris, France, having about 11 carbon atoms;

b. mixture similar to Isopar L manufactured by the U.S. Company Philips Petroleum Co. of Bartlesville, Oklahoma;

c. mixture of hydrocarbons of petroleum origin manufactured by the French Company ESSO Standard of Paris, France;

d. mixture of normal paraffin hydrocarbons produced by the British Company British Petroleum Chemicals Ltd. of London, England; e. mixture of normal paraffin hydrocarbons produced by the British Company British Petroleum Chemicals Ltd. of London, England;

f. mixture of normal paraffin hydrocarbons produced by the Swiss Company Schweizerische Sprengstoff-fabrik of Dottikon, Switzerland;

g. mixture of hydrocarbons of petroleum origin sold by American Mineral Spirits Co., Murray Hill, New Jersey;

h. mixture of hydrocarbons of petroleum origin sold by the U.S. Company Apco Oil Corporation of Oklahama City, Oklahoma;

j. mixture of hydrocarbons of petroleum origin produced by the U.S. Company Atlantic Refining Co., of Philadelphia, Pennsylvania. The preferred non-volatile higher alkanes are those which are found pure or in mixtures in nature; they can also be obtained by synthesis. When they are solid their melting point preferably ranges from 50° to 150°C. The following, which may be used alone or in mixtures, are given as non-limitative examples of preferred higher alkanes:

| | |
|---|---|
| n-octadecane | $C_{18}H_{38}$ |
| n-nonadecane | $C_{19}H_{40}$ |
| n-eicosane | $C_{20}H_{42}$ |
| n-heneicosane | $C_{21}H_{44}$ |
| n-docosane | $C_{22}H_{46}$ |
| n-tricosane | $C_{23}H_{48}$ |
| n-tetracosane | $C_{24}H_{50}$ |
| 2-methyl-tricosane | $C_{24}H_{50}$ |
| 2,2-dimethyl-docosane | $C_{24}H_{50}$ |
| 13-methyl-pentacosane | $C_{26}H_{54}$ |
| n-octacosane | $C_{28}H_{58}$ |
| 10-nonyl-nonadecane | $C_{28}H_{58}$ |
| n-triacontane | $C_{30}H_{62}$ |
| 2,6,10,15,19,23-hexamethyl-tetracosane | $C_{30}H_{62}$ (squalane) |
| n-hentriacontane | $C_{31}H_{64}$ |
| n-dotriacontane | $C_{32}H_{66}$ |
| n-tetratriacontane | $C_{34}H_{70}$ |
| n-pentatriacontane | $C_{35}H_{72}$ |
| n-hexatriacontane | $C_{36}H_{74}$ |
| n-tetracontane | $C_{40}H_{82}$ |
| n-tritetracontane | $C_{43}H_{88}$ |
| 22-methyl-tritetracontane | $C_{44}H_{90}$ |

Of the preferred mixtures of higher alkanes, there may be mentioned the liquid mixtures known as vaseline oil, paraffin oil, heavy oil, gas oil, fuel oil, road oil, valve oil, diesel oil; the semi-solid mixtures known as vasoline, petrolatum, crude paraffin; the micro-crystalline waxy mixtures (crystals finer than 5 microns) known as microwax, tank bottom wax, ozocerite, ceresine, isoparaffins; and the non-waxy, macrocrystalline solid mixtures (crystals larger than 5 microns) known as ordinary paraffin. The diluent (C) can further be selected from:

b. Aromatic hydrocarbons

The preferred compounds correspond to the following general formula

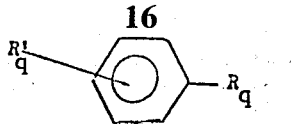

in which $R_q$ is hydrogen or alkyl of 1–5 carbon atoms and $R'_q$ represents one to three alkyl groups containing 1–4 carbon atoms located at any position on the benzene nucleus. $R_q$ and $R'_q$ can also represent together a saturated divalent hydrocarbon group containing 1–4 carbon atoms.

There are, for example mesitylene, tert-butylbenzene, pseudocumene, isobutylbenzene, sec-butylbenzene, n-butylbenzene, p-propyl-toluene, p-cymene, 1,4-diethyl benzene, p-tert-butyl-toluene, p-diisopropyl-benzene, tetraline, durene, isodurene, "Hi-sol 15" (a'), "Hi-sol 70" (b'), "Panasol RX-22" (c'), Amsco Solvent D (D'), Amsco Solvent F (e'), Solvarex 10 (f'), Solvesso 150 (g').

a'. mixture of aromatic hydrocarbons distilling between 177° and 216°C, produced by the U.S. Company of St. Louis (Missouri)

b'. mixture of aromatic hydrocarbons distilling between 168° and 202°C produced by the R. J. Brown Company noted above.

c'. mixture of aromatic hydrocarbons distilling between 186° and 211°C produced by the U.S. Company, Amoco Chemicals Corporation of Chicago (Illinois).

d'. mixture of aromatic hydrocarbons distilling between 165° and 196°C produced by the American Spirits Company already noted.

e'. mixture of aromatic hydrocarbons distilling between 177° and 204°C produced by the American Mineral Spiritis Company already noted.

f'. mixture of aromatic hydrocarbons distilling between 182° and 200°C produced by Compagnie Francaise de Raffinage of Paris.

g'. mixture of aromatic hydrocarbons distilling between 187° and 212°C.

c. Halogenated aliphatic hydrocarbons

The preferred compounds contain 6–14 carbon atoms in straight or branched chain and one atom of chlorine or bromine, or 2–8 carbon atoms in straight or branched chain and 2–6 chlorine atoms or 2–4 bromine atoms, one to three of these latter being replaceable with 1–4 chlorine atoms.

There are, for example, 1-chloro-octane,1-chlorononane, 1-chlorodecane, 1-chloroundecane, 1-chlorododecane, 1-bromoheptane, 1-bromo-octane, 1,3-dibromo-propane, 1,2-dibromobutane, 1,2,3-tribromopropane, hexachlorethane.

d. Halogenated aromatic hydrocarbons

The preferred compounds correspond to the following general formula

in which $R_r$ is hydrogen or alkyl of 1–5 carbon atoms and $R''_r$ represents one to three atoms of chlorine and/or bromine. There are, for example: 1,2-dichlorobenzene, 2-bromotoluene, 4-bromotoluene, chloro-4-ethyl benzene, aryldibromoethylbenzene (h').

e. Monoethers

The preferred compounds correspond to the following general formula:

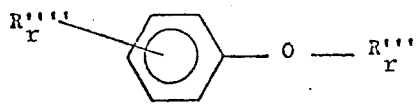

in which $R_r'''$ is alkyl of 1–6 carbon atoms and $R_r''''$ is halogen such as chlorine or bromine or an alkyl group of 1–4 carbon atoms. There is for example: phenetol, homophenetol, o-chloranisole, p-chloranisole, 4-methoxy toluene.

f. Diethers of the formula $$R_s - O - X - O - R_s'$$

wherein $R_s$ or $R_s'$ are the same or different and are alkyl of 1 to 6 carbons, X represents a divalent hydrocarbon group containing 1 to 6 carbons in straight or branched chain or is benzene.

g. Triethers of the formula $$R_a'' - Y_1 - O - Y' - O - R_a'''$$

wherein $R_a''$ and $R_a'''$ are the same or different and are alkyl of 1 to 5 carbons, Y and Y' are the same or different and are divalent hydrocarbon groups containing 1 to 3 carbons in straight or branched chain.

h. Triethers of the formula

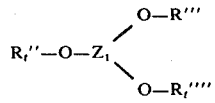

wherein $R_t''$, $R_t'''$ and $R_t''''$ are the same or different and are alkyl of 1 to 5 carbons, $Z_1$ represents a trivalent hydrocarbon group containing 1 to 3 carbons in branched or straight chain or is benzene.

i. Tetraethers of the formula $$R_u - O - Y_1 - O - Y' - O - Y'' - O - R'_u$$

in which $R_u$ and $R_u'$ are the same or different and an alkyl of 1 to 4 carbons, $Y_1$, $Y'$ and $Y''$ are the same or different and are divalent hydrocarbon groups of 1 to 3 carbons in straight or branched chain.

j. Pentaethers of the formula $$R_u'' - O - Y_1 - O - Y' - O - Y'' - O - Y''' - O - R_u'''$$

wherein $R_u''$ and $R_u'''$ are the same or different and are alkyl of 1 to 3 carbons, $Y_1$, $Y'$, $Y''$ and $Y'''$ are the same or different and are divalent hydrocarbon groups of 1 to 3 carbons in straight or branched chain.

k. Heterocyclic compounds of the formula

wherein X is O or S and $A_o$ is the divalent group butadiene-1,3-diyl or 1,4-butanediyl or 3-thia-1,5pentanediyl or 2-oxa-1,5-pentanediyl or 3-oxa-1,5-pentanediyl, which divalent group is either unsubstituted or substituted by phenyl and/or 1 or 4 alkyl substituents of 1 or 4 carbons. The diluents which can also be used in an evaporator system according to the instant invention are also the l. artifical hydrophobic cellulose derivatives (methyloxide, ethyloxide, benzyloxide, acetate, propionate, butyrate, phthalate, nitrate, etc.), m. solid synthetic organic resins such as homopolymers and copolymers orginating from vinyl derivatives (acetate, propionate, butyrate, oxides, formal, acetal, butyral, chloride, etc.) and/or vinylidene derivatives and/or alkenes (ethylene, propylene, butylene, etc.) and/or styrene and/or vinylpyrrolidones and/or isoprene and/or butadiene and/or acrylic or methacrylic esters and/or allyl esters (phthalate, isophthalate, maleate, cyanurate): or an "epoxy" resin obtained by the condensation of an epoxide and a polyphenol, a "polyester" resin obtained by the reaction of a polyacid with a polyol, a "polyurethan" resin obtained by the condensation of a polyisocyanate with a polyol, or a coumarone/indene resin; or n. natural rosin derivatives such as, for example, colophony, shellac or tallol or a waxy rosin.

The present invention is based on an unexpected discovery, which does not result from the known state of the art. The volatile phosphoric ester used in evaporators are in fact very sensitive to the action of organic compounds carrying at least one polar free group of the nature of an alcoholic hydroxy group. This results in partial decomposition of the esters, more or less rapid in time, and in consequence in a considerable reduction in the efficiency of the evaporator in which these esters and these alcoholic compositions are present. One advantageous feature of the invention resides therefore in the fact that, due to the high stabilizing power of the diazene compounds, polar and hydrophilic alcoholic compounds can now be used as solvent or otherwise, simultaneously with the phosphoric esters inside of an evaporator device. Some alcoholic compounds may be present fortuitously in insecticidal compositions. It is a matter, for example, of impurities contained in non-hydroxylated solvents or diluents used in the preparation of insecticidal compositions.

It follows from the foregoing that several alcoholic compounds may be found simultaneously in the evaporator, each one of them playing its own role, voluntarily or otherwise, and that the quantities incorporated are very variable.

Alcoholic compounds suitable as diluent (C) are "organic compounds containing at least one alcoholic hydroxyl group." Chemical classes comprised by this term are in particular:

1. saturated or unsaturated primary, secondary or tertiary aliphatic alcohols
2. saturated or unsaturated alicyclic alcohols
3. aralkanols and aralkenols
4. glycols and their monoesters and monoethers
5. partially esterified and/or etherified polyols The alcoholic compounds are chosen with regard to the value intended for them in the evaporator. Indeed, they may be incorporated a. as principal solvents or diluents of the phosphoric ester or esters used or as solvent of the diazene, b. as supplementary reinforcing solvents (co-solvents) to non-hydroxyl solvents or diluents for the phosphoric ester or esters, or for the diazene, c. as odorant products, such as natural or synthetic odorants or perfumes as geraniol, linalol, terpineol, menthol and citronellol, or compositions containing one or more of these odorant materials.

Especially the alcoholic compounds envisaged by the invention as solvents are liquids or solids having a low melting point.

Their vapour pressure at 20°C is preferably between 0.01 and 30 Torr, and more preferably between 0.01 and 5 Torrs. This corresponds generally to products distilling at atmospheric pressure, between 100° and 320°C, preferably between 140° and 270°C.

Preferably these alcoholic compounds belong to the following categories:

−1° Primary, secondary or tertiary, saturated or non-saturated, aliphatic hydroxylated compounds corresponding to the following general formula:

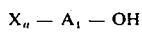

wherein $X_a$ represents a hydrogen atom or a chlorine atom or an alkylthio or alkoxy group containing 1 to 10 carbon atoms or an alkoxyalkoxy group containing 2 to 6 carbon atoms. $A_1$ represents a divalent, straight or branched-chain hydrocarbon group containing 2 to 6 carbon atoms which number may be up to 20 carbon atoms when $X_a$ represents a hydrogen atom. Such hydroxylated acyclic compounds are, for example, the following: 2-methoxy-ethanol, 2-ethoxy-ethanol, 2-butoxy-ethanol, methanol, ethanol, propanol, isopropanol, butanol, isobutanol, sec-butanol, tert-butanol, pentanol, isopentanol, hexanol, octanol, sec-octanol, decanol, undecanol, dodecanol, tetradecanol, hexadecanol, octadecanol, octadec-9-en-1-ol, undec-10-en-1-ol, 2-ethyl-hexan-1-ol, 3,7-dimethyl-octan-1-ol, linalool, nerol, geraniol, citronellol, hex-3-en-1-ol, 3,6-dioxa-octan-1-ol, 3,6-dioxa-nonan-1-ol 3,6-dioxa-decan-1-ol, hydroxyethylthiooctane, allyl alcohol, 2-chloro-ethanol.

−2° Alicyclic hydroxylated compounds corresponding to the following general formula:

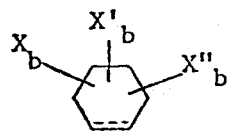

wherein $X_b$ represents a hydrogen atom or one to four alkyl radicals containing 1 to 5 carbon atoms; $X'_b$ represents a hydrogen atom or an alkenyl radical containing 2 to 4 carbon atoms; $X''_b$ represents a hydroxy group or a hydroxyalkyl group containing 1 to 5 carbon atoms; the dotted line represents an optional second bond.

Such alicyclic hydroxylated compounds are, for example, the following: cyclohexanol, 3-methyl-cyclohexanol, 3,3,5-trimethyl-cyclohexanol, menthol, α-terpineol, β-terpineol, and γ-terpineol.

−3° Araliphatic alcohols being aralkanols or aralkenols corresponding to the following general formula:

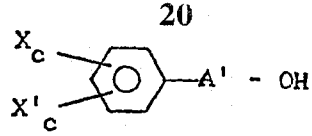

wherein $A'$ represents a saturated or ethylenically unsaturated, straight or branched-chain aliphatic hydrocarbon group containing up to 5 carbon atoms; $X_c$ represents a hydrogen atom or 1 to 5 halogen atoms selected from chlorine or bromine; $X'_c$ represents a hydrogen atom or 1 to 3 alkyl radicals containing 1 to 6 carbon atoms, (the total number of $X_c + X'_c$ naturally not exceeding five).

Such aromatic alcohols are, for example, the following: benzyl alcohol, 2-phenyl-ethanol, 1-phenyl-ethanol, 1-phenyl-propan-1-ol, 1-phenyl-propan-2-ol, 3-phenyl-propan-1-ol, cinnamic alcohol, p-methylcinnamic alcohol, p-chlorobenzyl alcohol, p-methylbenzyl alcohol, dichlorophenylethanol, pentachlorobenzyl alcohol.

−4° Polyols corresponding to the following general formula:

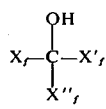

wherein $X_f$ represents either an alkyl radical having 1 to 6 carbon atoms and substituted by 1 to 5 hydroxy groups, said radical being optionally further substituted by a phenyl, chlorophenyl or nitrophenyl radical, or an alkanoylamino group having 2 to 6 carbon atoms and which may be substituted by 1 to 3 chlorine atoms; $X'_f$ represents a hydrogen atom or an alkyl radical having 1 to 6 carbon atoms or a phenyl radical which may be optionally substituted by 1 to 3 chlorine atoms and/or by a nitro group; $X''_f$ represents a hydrogen atom or an alkyl radical having 1 to 4 carbon atoms and optionally substituted by 1 to 3 chlorine atoms.

Such polyols are for example the following: propane-1,2-diol, ethylene-glycol, propylene-glycol, glycerol, glycerol-α-chlorohydrin, glycerol-β-chlorohydrin, sorbitol, 2-ethyl-hexane-1,3-diol (k), an insect repellent known as Ethohexadiol, 2-butyl-2-ethyl-propane-1,3-diol, Chlorampenicol.

−5° Esters of the above polyols having at least one free hydroxy group and formed from saturated or ethylenically unsaturated aliphatic acids having 2 to 20 carbon atoms.

−6° Oxirane condensation products (alkylene oxides) corresponding to the general formula:

$$X_j - O - (A'' - O)_n - A'' - OH$$

wherein $A''$ represents a straight or branched-chain, saturated aliphatic hydrocarbon group having 1 to 4 carbon atoms; n represents a whole number from 1 to 150; $X_j$ represents a hydrogen atom or an alkyl radical containing 1 to 6 carbon atoms or an alkanoyl or alkenoyl group having 2 to 20 carbon atoms.

Such oxirane condensation products are, for example, the following: diethylene glycol, triethylene glycol, dipropylene glycol, tripropylene glycol, dibutylene glycol, polyethylene glycols having a molar mass of from 200 to 6000 gram moles, polypropylene glycols having a molar mass of from 200 to 6000 gram moles, monolaurates, monopalmitates, monostearates and monooleates of these glycols; methyl, ethyl, propyl and butyl monoethers of these glycols.

In addition to the latter category, there may be mentioned the oxyalkylenated, partially esterified derivatives of sorbitan, such as the monolaurate, monopalmitate, monostearate, monooleate, trioleate and tristearate of sorbitan, condensed with 4 to 20 moles of ethylene oxide, and unesterified condensation products of sorbitan and 4 to 20 moles of ethylene oxide.

Especially preferred alcoholic compounds belong to the groups hereafter noted, for each of which non-limitative examples have been given.

1a. Aliphatic alcohols falling under the general formula

wherein $R_{t'}$ represents hydrogen or alkoxy of 1–6 carbon atoms or alkoxyalkoxy of 2–6 carbon atoms, $A_2$ is a straight or branched chain hydrocarbon group of 1–6 carbon atoms, this number being able to be raised to 14 carbon atoms when $R_{t'}$ is hydrogen.

Examples are: 2-butoxyethanol, 1-octanol, 2-octanol, 1-heptanol, 2-ethyl-1-hexanol, 3,6-dioxa-1-octanol, 3,6-dioxa-1-nonanol, linalol, 3,7-dimethyl-1-octanol.

2a. Alicyclic alcohols falling under the general formula

in which $R_w$ is hydrogen or one to four alkyl groups of 1–5 carbon atoms.

Examples are: 3-methylcyclohexanol, menthol, 3,3,5-trimethyl cyclohexanol;

3a. Aralkanols falling under the general formula

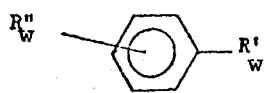

wherein $R_w'$ is hydroxyalkyl of 1–5 carbon atoms, and $R_w''$ represents one to three atoms of chlorine and/or one to two alkyl groups of 1–4 carbon atoms. 1-Phenyl-2-propanol is an example of this type of compound.

The amounts of the alcoholic compounds contained in the instant evaporator system can be varied greatly; in particular, one or more of these compounds can be used as the sole solvent for the phosphoric acid ester used in practice and/or for the diazene; one or more of these compounds can be used as co-solvent; one or more alcoholic compounds usually having a low molecular mass may also be contained among the impurities in the non-hydroxylated solvent or solvents used in the evaporator system according to the instant invention.

The evaporator system according to the invention can also optionally comprise inert mineral additives, which are for example the following: brick, pumice, vermiculite, kaolin, dry clay, calcium carbonate, pyrophyllite, dolomite, glass fibres, plaster of Paris, talcum, fossil or non-fossil natural silica, synthetic silica, and metallic oxides; or inert organic additives which are, for example pigments, wood dust, cellulose fibres, starch, dextrin, sugars, thickening agents such as aluminum salts of higher aliphatic acids and/or salts formed from alkylamines and a montmorillonite.

The evaporator can be of any known type, for example it can be a wick evaporator or a shaped solid body, or an impregnated sheet or plate consisting in a solid porous or fibrous support such as for example, paper, wool felt, cotton, synthetic fibres, compressed cellulose such as wood fibers, cereals, alfa and cotton, felt cardboard, or board made of old paper or glass fibres.

The presence of a diazene stabilizer confers to the phosphoric acid ester an increased resistance to the destructive effect of water and/or of an alcoholic compound contained in the composition and of the ambient humidity, as is shown in the following experiments which are given by way of example.

Some experiments carried out by the Applicants are given hereinafter to afford a better comprehension of the preceding statements.

EXPERIMENT A

A specimen of the compound obtained by a coupling β-naphthol and diazotized o-anisidine, the compound generally known as 1-(2-methoxy-phenylazo)-2-naphthol (a), is dissolved in deuteriochloroform to form a saturated solution and then used in a nuclear magnetic resonence spectrometer, model DP 60 made by the American company Varian Associates, Palo Alto, Calif. U.S.A. Tetramethylsilane was used as reference compound.

a. This compound can also be obtained by reacting anisyl hydrazine and naphthoquinone.

The spectrogram obtained shows a singlet corresponding to three protons of the methoxy group suitably located in the region of high field strength and a multiplet showing 11 protons in the region of low field strength. There was no isolated peak representing a phenolic proton; all attempts to modify the spectrum by the addition of deuteriotrifluoracetic acid failed and in no case was a phenolic proton suggested outside the multiplet.

The experiment shows that, under the conditions used for the experiment, this compound does not have an oyxazoic structure, but, more probably, a hydrazonoquinonic structure; in order to take this into account, this compound is designated, in the instant specification, by the name 1-(2-methoxy-phenylhydrazono)-1,2-dihydro-2-oxo-naphthalene.

EXPERIMENT B

The procedure of Experiment A was followed using a saturated solution in deuteriochloroform of the compound obtained from coupling β-naphthol and diazotized xylidine, this compound being known as 1-xylylazo-2-naphthol (b). The spectrograms obtained showed the presence of two methyl groups in the region of high field strength, while the other 10 protons appeared in multiplet in the region of low field strength. No isolated peak representing a phenolic proton appeared even after the addition of deuterio-trifluoracetic acid.

b. This compound can also be obtained by reacting xylylhydrazine with naphthoquinone.

Here again, this experiment shows that the compound studied does not, under the conditions used for the experiment, have the oxyazoic structure which is usually given to it but rather a hydrazonoquinonic structure; for this reason, it is designated in the instant specification as 1-xylylhydrazono-1,2-dihydro-2-oxo-naphthalene.

The two preceding experiments show that a compound known by a name based on an azoic structure (diazenylene) can, in reality, at least under certain conditions, not have that structure, but rather a hydrazonic structure (diazanylidene), in particular when that compound is obtaind from a coupling reaction in which one of the reactants is a phenol (or naphthol); furthermore, as it is possible and recognized that most of these compounds, depending on the medium of the conditions present, can pass from one tautomeric form to the other and this being generally reversible, it is understood that the designations employed in the instant specification comprise all the tautomeric forms of the compounds concerned.

EXPERIMENT C

Squares, 10 × 10 centimeters, cut from a cellulose cardboard, manufactured by the French company Fioroni S.A. under the refererence No. 200, are used; at the time of use, the cardboard weighed 860 grams per square meter, i.e. 8.6 grams per square; the amount of free water per square, determined by means of an infrared hygrometer, was 0.4 g.

The cardboard squares were arranged in four series of three each, designated as C - 0 to C - 3; the squares C - 0 were impregnated with 17 grams of DDVP and the other squares were impregnated with 17 grams of a 1 percent solution of one of the following compounds in the DDVP:

C - 1: phenylhydrazonocyclohexane (c)
C - 2: 2-(2,4-dinitro-phenylhydrazono)-propane (c')
C - 3: (2,4-dinitro-phenylhydrazono)-cyclohexane (c'')
  c. compound obtained from the reaction of phenylhydrazine and cyclohexanone
  c'. compound obtained from the reaction of 2,4-dinitro-phenylhydrazine and acetone
  c''. compound obtained from the reaction of 2,4-dinitro-phenylhydrazine and cyclohexanone.

The squares thus impregnated were suspended in a room in which the temperature was kept at 20 ± 2°C and the relative humidity was about 45.

At the end of 15 days, the amount of DDVP destroyed by hydrolysis was measured potentiometrically (it has been found, furthermore, that the hydrolysis of DDVP under the above-given conditions leads to an acid phosphoric ester and that the potentiometric measure of the sole acidity or of the first acidity of the acid ester indicates the amount of DDVP which hydrolyzed).

Account was taken of the acidity present in the DDVP (0.4% of the equivalent weight of DDVP), which acidity was deducted from the results obtained.

The percentage amounts of DDVP decomposed by hydrolysis which were determined are tabulated in the following table; (the values indicated by the sign ± give the range in which the results deviate in each series);

| C - 0 | C - 1 | C - 2 | C - 3 |
|---|---|---|---|
| 31.3 ± 1.0 | 6.5 ± 0.5 | 12.2 ± 0.3 | 13.4 ± 0.6 |

The results of this experiment show clearly to what extent DDVP is sensitive to humidity when it is not protected; it also shows that hydrolysis can be reduced by a considerable amount when a diazene known to have a hydrazonic structure (diazanylidene) is added to the phosphoric acid ester.

EXPERIMENT D

Cardboard squares as described in Experiment C were used, but the unit weight thereof was 8.85 g, of which 0.65 g was water. The squares were arranged in four series of three each, designated as D - 0 to D - 3; the squares D - 0 were impregnated with 17 grams of DDVP and the other squares were impregnated with 17 grams of a 1 percent solution of one of the following compounds in the DDVP:

D - 1: (4-chloro-phenylhydrazono)cyclohexane (d)
D - 2: 1-(2,4-dinitro-phenylhydrazono)-3,5,5-trimethyl-2-cyclohexene (d')
D - 3: 3-(4-nitro-phenylhydrazono)-2-indolone (d'')
  d. compound obtained from the reaction of 4-chloro-phenylhydrazine and cyclohexanone.
  d'. compound obtained from the reaction of 2,4-dinitro-phenylhydrazine and isophorone
  d''. compound obtained from the reaction of 4-nitro-phenylhydrazine and isatin.

The squares thus impregnated were suspended in a room in which the temperature was kept at 20 ± 2°C and the relative humidity was about 65.

At the end of 10 days, the percentage amounts of DDVP destroyed were measured as described in Experiment C and tabulated as follows:

| D - 0 | D - 1 | D - 2 | D - 3 |
|---|---|---|---|
| 35.3 ± 1.3 | 5.1 ± 0.3 | 8.2 ± 0.1 | 4.2 ± 0.3 |

The results of the present experiment confirm those of the preceding experiment for other diazenes having an analogous structure, in the case of a higher humidity of 65%.

EXPERIMENT E

Cardboard squares as described in Experiment C were used, but the unit weight thereof was 8.80 g, of which 0.60 g was water. The squares were arranged in two series of three each, designated as E - 0 and E - 1; the squares E - 0 were impregnated with 17 g of DDVP and the other squares were impregnated with 17 g of a 1% solution of the compound known as azobenzene (e). The squares thus impregnated were suspended in a room in which the temperature was kept at 24° ± 2°C and the relative humidity was about 60. At the end of 10 days, the percentage amounts of DDVP destroyed were measured as described in Experiment C and tabulated as follows:

| E - 0 | E - 1 |
|---|---|
| 25.6 ± 0.7 | 0.8 ± 0.1 | e. compound obtained from the reduction of nitrobenzene in an alkaline medium.

EXPERIMENT F

Cardboard squares as described in the preceding experiments were used, the unit weight thereof being 8.85 g, of which 0.65 g was water. The squares were arranged in four series of three each, designated as F - 0 to F - 3; the squares F - 0 were impregnated with 17 g of DDVP and the other squares were impregnated with 17 g of a 1% solution of one of the following compounds in the DDVP:

F - 1: azophenetol (f)
F - 2: 4-phenylazo-benzoic acid
F - 3: 1-(4-ethoxy-phenylazo)-4-heptanoyloxy-benzene
f. compound obtained from the reduction of 4-nitro-phenetol in an alkaline medium.

The squares thus impregnated were suspended in a room in which the temperature was kept at 22 ± 2°C and the relative humidity was about 65.

At the end of 15 days, the percentage amounts of DDVP destroyed were measured as described in Experiment C and tabulated as follows:

| F - 0 | F - 1 | F - 2 | F - 3 |
|---|---|---|---|
| 38.5 ± 1.0 | 3.2 ± 0.6 | 18.3 ± 0.8 | 2.4 ± 0.3 |

The results of Experiments E and F show that the hydrolysis of DDVP can be greatly reduced when a diazene known to have an azoic structure (diazenylene) is added to this phosphoric acid ester. Furthermore, it is noted that the presence of functional substituents such as alkoxy, carboxy or alkanoyloxy groups does not hinder the effectiveness of the compounds contemplated by the invention; this effectiveness, however, seems to be slightly less when the diazene is substituted by a carboxy group.

EXPERIMENT G

Cardboard squares as described in the preceding experiments were used, the unit weight thereof being 8.60 g, of which 0.40 g was water. The squares were arranged in seven series of three each, numbered G - 0 to G - 6; the squares G - 0 were impregnated with 14.2 g of DDVP and the other squares were impregnated with 14.2 g of a 1% saturated solution in DDVP of an oxyazo dyestuff the solubility of which in DDVP being from 0.2 to 1%; the compounds used were the following:

G - 1: 1-(4-phenylazo-phenylhydrazono)-1,2-dihydro-2-oxo-naphthalene (g)
G - 2: 1-(2-methoxy-phenylhydrazono)-1,2-dihydro-2-oxo-naphthalene (g')
G - 3: 1-xylylhydrazono-1,2-dihydro-2-oxo-naphthalene (g'')
G - 4: 1-(4-o-tolylazo-2-methyl-phenylhydrazono)-1,2-dihydro-2-oxo-naphthalene (g''')
G - 5: 1-phenylhydrazono-1,2-dihydro-2-oxo-naphthalene (g'''')
G - 6: 1-(2-pyridyl-hydrazono)-1,2-dihydro-2-oxo-naphthalene (g''''')
g. compound obtained coupling β-naphthol and diazotized 4-aminoazobenzene; this compound is often designated 1-(4-phenylazo-phenylazo)-2-naphthol corresponding to its azoic form;
g'. compound already cited in Experiment A;
g''. compound already cited in Experiment B;
g'''. compound obtained from coupling β-naphthol and diazotized 4-amino-2',3-dimethyl-azobenzene; this compound is often designated 1-(4-o-tolylazo-2-methyl-phenylazo)-2-naphthol corresponding to its azoic form;
g''''. compound obtained from coupling β-naphthol and diazotized aniline; this compound is often designated 1-phenylazo-2-naphthol corresponding to its azoic form; it can also be obtained by reacting phenylhydrazine and naphthoquinone;
g'''''. compound obtained by coupling β-naphthol and diazotized 2-amino-pyridine; this compound is often designated 1-(2-pyridyl-azo)-2-naphthol corresponding to its azoic form.

The squares thus impregnated were suspended in a room in which the temperature was kept at 22 ± 2°C and the relative humidity was about 35.

At the end of 12 days, the percentage amounts of DDVP destroyed were measured as described in Experiment C and tabulated as follows:

| G - 0 | G - 1 | G - 2 | G - 3 | G - 4 | G - 5 | G - 6 |
|---|---|---|---|---|---|---|
| 23.0 ± 0.6 | 2.1 ± 0.1 | 3.3 ± 0.3 | 4.4 ± 0.3 | 3.4 ± 0.3 | 1.1 ± 0.1 | 0.9 ± 0.1 |

The results of this experiment show that the hydrolysis of DDVP is greatly reduced when a diazene belonging to the family of "oxyazo" dyestuffs is added to this phosphoric acid ester; it is noted that one of the substituents of the diazene group can be a heterocycle such as pyridine without diminishing the effectiveness.

EXPERIMENT H

Cardboard squares as described in the preceding experiments were used, the unit weight thereof being 8.75 g, of which 0.55 g was water. The squares were arranged in three series of three each, designated H - 0, H - 1 and H - 2; the squares H - 0 were impregnated with 17 g of DDVP and the other squares were impregnated with 17 g of 1% solution of one of the following compounds in the DDVP:

H - 1: 1-(4-ethoxy-phenylhydrazono)-1,4-dihydro-4-oxobenzene (h)
H - 2: 1-(4-ethoxy-phenylazo)-4-heptanoyloxy-benzene (h')
h. compound obtained from coupling phenol and diazotized 4-amino-phenetol; this compound is often designated 4-(4-ethoxy-phenylazo)-phenol corresponding to its azo form;
h'. compound corresponding to the ester formed from heptanoic acid and the preceding compound considered in its azo form.

The squares thus impregnated were suspended in a room in which the temperature was kept at 20 ± 2°C and the relative humidity was about 55.

At the end of 10 days, the percentage amounts of DDVP destroyed were measured as described in Experiment C and tabulated as follows:

| H - 0 | H - 1 | H - 2 |
|---|---|---|
| 19.2 ± 0.8 | 3.5 ± 0.6 | 1.0 ± 0.1 |

The results of this experiment concerning H - 1 confirm those noted in Experiment G; they show, furthermore, that the quinone function (or phenol in the form considered as being azo) does not have any stabilizing effect; the esterified compound seems to have an even more significant effect; if the first compound had two stabilizing functions, this would be contrary to that which has been found.

EXPERIMENT I

Cardboard squares as described in the preceding experiments were used, the unit weight thereof being 8.60 g, of which 0.40 g was water. The squares were arranged in three series of three each, numbered I - 0 to I - 3; the squares I - 0 were impregnated with 14.2 g of DDVP and the other squares were impregnated with 14.2 g of a solution in DDVP of one of the following compounds in the percentages indicated below:

I - 1: 1% of 1-(4-phenylazo-phenylazo)-2-ethylaminonaphthalene (i)

I - 2: 0.5% of 1-(1-phenylazo-4-naphthylazo)-4-ethylaminonaphthalene (i')

I - 3: 0.5% of 6-(1-phenylazo-4-naphthyl-azo)-2,3-dihydro-2,2-dimethyl-perimidine (i'')

i. compound obtained from coupling 2-ethylaminonaphthalene and diazotized 4-amino-azobenzene; this compound can also be considered to be 1-(4-phenylazo-phenylhydrazono)-1,2-dihydro-2-ethylimino-naphthalene corresponding to its hydrazono form;

i'. compound obtained from coupling 1-ethylaminonaphthalene and diazotized 1-amino-4-phenylazo-naphthalene; this compound can also be considered to be 1-(1-phenylazo-4-naphthyl-hydrazono)-1,4-dihydro-4-ethylimino-naphthalene corresponding to its hydrazono form;

i''. compound obtained from coupling 2,3-dihydro-2,2-dimethylperimidine and diazotized 1-amino-4-phenylazo-naphthalene.

The squares thus impregnated were suspended in a room in which the temperature was kept at 22 ± 2°C and the relative humidity was about 35.

At the end of 12 days, the percentage amounts of DDVP destroyed were measured as described in Experiment C and tabulated as follows:

| I - 0 | I - 1 | I - 2 | I - 3 |
|---|---|---|---|
| 23.0 | 3.8 | 4.2 | 2.2 |
| ± 0.6 | ± 0.3 | ± 0.2 | ± 0.2 |

The results of this experiment show that the hydrolysis of DDVP can be considerably reduced when a diazene of the family of "basic azo" dyestuffs is added to this phosphoric acid ester.

EXPERIMENT J

Cardboard squares as described in the preceding experiments were used, the unit weight thereof being 8.85 g, of which 0.65 g was water.

The squares were arranged in two series of three each, designated J - 0 and J - 1; the squares J - 0 were impregnated with 17 g of DDVP and the squares J - 1 were impregnated with 17 g of a 1% solution of 1,3,5-triphenyl-1,2,4,5-tetraza-1,3-pentadiene (j) in DDVP.

j. compound known as triphenylformazan-, phenylformazyl- or formazylbenzene- α-phenylazo-α-phenylhydrazono-toluene.

The squares thus impregnated were suspended in a room in which the temperature was kept at 22 ± 2°C and the relative humidity was about 65.

At the end of 15 days, the percentage amounts of DDVP destroyed were measured as described in Experiment C and tabulated as follows:

| J - 0 | J - 1 |
|---|---|
| 38.5 | 0.8 |
| ± 1.0 | ± 0.1 |

The results of this experiment illustrate the case where the stabilizers contemplated by the invention have two diazene groups forming a formazyl compound.

EXPERIMENT K

Cardboard squares as described in the preceding experiments were used, the unit weight thereof being 8.60 g, of which 0.40 g was water. The squares were arranged in seven series of three each designated K - 0 to K - 6; the squares K - 0 were impregnated with 14.2 g of DDVP and the other squares were impregnated with 14.2 g of 1% solution of the following metal complex compounds in DDVP:

K - 1: (1:2) chromium complex of 4-(2-hydroxy-4-nitro-5-methylsulfonyl-phenylazo)-3-methyl-1-phenyl-5-pyrazolone, sodium salt K - 2: (1:2) chromium complex of 4-(2-hydroxy-3-nitro-5-tert-amyl-phenylazo)-3-methyl-1-phenyl-5-pyrazolone, sodium salt K - 3: (1:2) chromium complex of 4-(2-hydroxy-4-nitrophenylazo)-3-methyl-1-phenyl-5-pyrazolone, sodium salt K - 4: (1:2) cobalt complex, in equimolar mixture, of the diazo derivative of (2-amino-4-ethylsulfonyl-phenol) → 2-naphthol and the diazo derivative of (2-amino-4-ethylsulfonyl-phenol) → 2-(N-methoxycarbonyl-N-methylamino)-6-naphthol, sodium salt K - 5: (1:2) chromium complexes, in equivalent mixture, of the following azo compounds:
1-(2-hydroxy-5-nitro-phenylazo)-2-naphthol, sodium salt
1-(2-hydroxy-4-nitro-phenylazo)-2-naphthol, sodium salt
1-(2-hydroxy-3-nitro-5-tert-amyl-phenylazo)-2-naphthol, sodium salt K - 6: (1:2) chromium complexes, in equivalent mixture, of diazo-(2-amino-5-nitro-4-ethylsulfonyl-phenol) → 2-(2-carboxy-phenyl)-naphthylamine, sodium salt and diazo-(2-amino-5-nitro-4-ethylsulfonyl-phenol) → 8-hydroxy-quinoline, sodium salt.

The squares thus impregnated were suspended in a room in which the temperature was kept at 22 ± 2°C and the relative humidity as about 35.

At the end of 12 days, the percentage amounts of DDVP destroyed were measured as follows:

| K - 0 | K - 1 | K - 2 | K - 3 | K - 4 | K - 5 | K - 6 |
|---|---|---|---|---|---|---|
| 23.0 | 5.8 | 5.5 | 5.8 | 5.8 | 4.1 | 3.3 |
| ± 0.6 | ± 0.2 | ± 0.1 | ± 0.2 | ± 0.1 | ± 0.3 | ± 0.1 |

The results of this experiment show that the hydrolysis of DDVP can be considerably reduced when a metal complex compound derived from a diazene of the class of "azo" dyestuffs is added to this phosphoric acid ester.

EXPERIMENT L

Cardboard squares as described in the preceding experiments were used, the unit weight thereof being 8.75 g, of which 0.55 g was water. These squares were impregnated with 14.2 g of a solution containing 400 ppm of a diazene in DDVP. Sixteen squares thus treated were designated L - 1 to L - 16; one square was impregnated with DDVP with diazene and designated L - 0. The diazenes used were the following:

L - 1: azobenzene (e)
L - 2: 1-(4-phenylazo-phenylhydrazono)-1,2-dihydro-2-oxo-naphthalene (g)
L - 3: 1-xylylhydrazono-1,2-dihydro-2oxo-naphthalene (g")
L - 4: 1-(4-o-tolylazo-2-methyl-phenylhydrazono)-1,2-dihydro-2-oxo-naphthalene (g''')
L - 5: 1-(α-naphthylhydrazono)-1,2-dihydro-2-oxo-naphthalene (1)
L - 6: α,α-bis-[4-(1,4-dihydro-3-methyl-4-oxo-phenylidenehydrazo)-xylyl]-toluene (1')
L - 7: 1-(2-methoxy-phenylhydrazono)-1,2-dihydro-2-oxonaphthalene (g')
L - 8: 1-(1-phenylazo-4-naphthyl-azo)-4-ethylamino-naphthalene (i')
L - 9: 1-(4-phenylazo-phenylazo)-2-ethylamino-naphthalene (i)
L - 10: 6-(1-phenylazo-4-naphthyl-azo)-2,4-dihydro-2,2-dimethyl-perimidine (i")
L - 11: (1:2) cobalt complex, in equimolar mixture, of diazo-(2-amino-4-ethylsulfonyl-phenol) → 2-napththol and diazo-(2-amino-4-ethylsulfonyl-phenol) → 2-(N-methoxycarbonyl-N-methyl-amino)-7-naphthol, sodium salt
L - 12: (1:2) chromium complexes, in equivalent mixture, of the following azo compounds:
1-(2-hydroxy-5-nitro-phenylazo)-2-naphthol, sodium salt
1-(2-hydroxy-4-nitro-phenylazo)-2-naphthol, sodium salt
1-(2-hydroxy-3-nitro-5-ter-amyl-phenylazo)-2-naphthol, sodium salt
L - 13: (1:2) chromium complexes, in equivalent mixture, of diazo-(2-amino-5-nitro-4-ethylsulfonyl-phenol) → 2-(2-carboxy-phenyl)-naphthylamine, sodium salt and diazo-(2-amino-5-nitro-4-ethylsulfonyl-phenol) → 8-hydroxy-quinoline, sodium salt
L - 14: (1:2) chromium complex, in equivalent mixture, of 1-(2-hydroxy-5-nitro-phenylazo)-2-naphthol and 4-(2-hydroxy-5-nitro-phenylazo)-3-methyl-1-phenyl-5-pyrazolone, sodium salt
L - 15: (1:2) chromium complex of 1-(2-hydroxy-4-nitrophenylazo)-2-naphthol
L - 16: (1:2) cobalt complex of 1-(2-hydroxy-5-sulfamoylphenylazo)-2-naphthol.
1. compound obtained by coupling β-naphthol and diazotized α-naphthylamine; this compound is often designated as 1-(α-naphthylazo)-2-naphthol
1'. compound obtained by coupling 2 moles of o-cresol and the bis-diazotation product of α,α-bis-(4-amino-p-xylyl)-toluene; this compound is often designated as α,α-bis-[4-(4-hydroxy-3-methyl-phenylazo)-xylyl]-toluene, corresponding to its azo form.

The squares thus impregnated were suspended in a room in which the temperature was kept at 22 ± 2°C and the relative humidity was about 40.

At the end of 12 days, the percentage amounts of DDVP destroyed were measured as described in Experiment C and tabulated as follows:

| L - 0 | L - 1 | L - 2 | L - 3 | L - 4 | L - 5 | L - 6 | L - 7 | L - 8 |
|---|---|---|---|---|---|---|---|---|
| 37.0 | 14.2 | 16.8 | 23.5 | 22.2 | 23.9 | 25.0 | 29.9 | 23.1 |
| L - 9 | L - 10 | L - 11 | L - 12 | L - 13 | L - 14 | L - 15 | L - 16 | |
| 23.6 | 19.8 | 24.6 | 24.8 | 22.8 | 26.5 | 23.8 | 29.0 | |

The results of this experiment show that the stabilizing influence of the diazenes contemplated by the invention is noticeable even at a concentration as low as 400 ppm.

EXPERIMENT M

Square pieces, 10 × 10 centimeters, cut from a felt cardboard sold by the French company Mulner & Joncquez under the reference No. J-2-A-60, were used; these squares were each impregnated with 15 g of one of the formulations given below. The impregnated squares were joined in groups of two and placed in a sandwich between two pieces, having the same dimensions, cut from a cardboard, one side of which had been coated by a 23 micron layer of low density polyethylene, manufactured by the French company Papiethylene; the coated side faced outwards.

The edges of the whole were kept hermetic by welding together the two parts of a polyethylene frame. The evaporating devices thus obtained were arranged in four series designated M - 0, M - 1, M - 2 and M - 3 differing from one another by the impregnating formulations as follows:

| | M - 0 | M - 1 | M - 2 | M - 3 |
|---|---|---|---|---|
| DDVP | 85% | 75% | 85% | 75% |
| dioctyl phthalate | 15% | 25% | 14.5% | 24.5% |
| diazene metal complex (k) | -- | | 0.5% | 0.5% | k. chromium complex given in Experiment K (K - 5)

After storing for 7 days at 40°C, the evaporators were put into operation in a room in which the temperature was kept at 19 ± 1°C and the relative humidity was 70 ± 5.

At the end of 7 weeks of use, the amount of DDVP destroyed was measured as described in Experiment C, giving the following values (in grams):

| M - 0 | M - 1 | M - 2 | M - 3 |
|---|---|---|---|
| 8.8 ± 0.8 | 7.4 ± 0.3 | 0.8 ± 0.1 | 0.5 ± 0.2 |

These results obtained from the use of an evaporator in practice confirm those obtained in the preceding experiments.

EXPERIMENT N

Wick evaporators comprising a reservoir and a felt wick one end of which ends at the bottom of the reservoir and the other is joined to a felt disk having an evaporating surface of 60 cm²; the wick and the disk are made from a wool felt, quality 13 A, manufactured by the French company Sommer.

The devices were arranged in four series designated N - 0, N - 1, N - 2 and N - 3, of 5 devices each; the pieces of felt were completely dried before being put into place.

The devices of the series N - 0 and N - 2 were provided with white felt disks; the devices of the series N - 1 and N - 3 were provided with black felt disks, the dye of which being insoluble in the solution defined below.

To the devices of the series N - 0 and N - 1 there were added 50 g each of a 9 percent solution of DDVP in a mixture of inert aliphatic hydrocarbon solvents having a vapor tension at 20°C of about 0.4 Torr; the devices of the series N - 2 and N - 3 received the same solution containing in addition 0.1 g of (1-(4-phenylazo-phenylazo)-2-N-ethylamino-naphthalene (i).

The amount of water present in the solvent mixture was 5 milligrams, corresponding to a potential destruction of 61 mg of DDVP. The evaporators thus prepared were placed in use in a room in which the temperature was kept at 22 ± 2°C and the relative humidity was about 50.

At the end of one month, the amount of DDVP destroyed by hydrolysis, corresponding to the difference between the initial acidity and the acidity found after use, was tabulated as follows (in milligrams):

| N - 0 | N - 1 | N - 2 | N - 3 |
|-------|-------|-------|-------|
| 63    | 58    | 15    | 12    |
| ± 10  | ± 10  | ± 3   | ± 2   |

This experiment shows that when no stabilizer as contemplated by the invention is present, the total water present in the solvent mixture acts to hydrolyse the DDVP, whereas when such a stabilizer is present only 20 to 25 percent of the amount of water present enters the reaction. Furthermore, this experiment shows that the insoluble black dye of the felt has practically no stabilizing influence; therefore the stabilization is, in fact, a chemical one due to the diazene function and not an optical protection due to the color of the stabilizer.

EXPERIMENT P

Squares, 10 × 10 centimeters, cut from a wool felt of the quality 13 A cited above having an average thickness of 3 millimeters, were used; this felt was dyed red by the manufacturer, who verified that the dyestuff used was insoluble in DDVP.

The squares were dried for one hour at 110°C and then arranged in four series of three each, designated P - 0 to P - 3; a series marked P - 00 was prepared from undyed felt of the same quality and dried in the same manner.

The squares P - 0 and P - 00 were impregnated with 22.5 g of DDVP and the other squares were impregnated with 22.5 g of a 1 percent solution of one of the following compounds in DDVP:

P - 1: 1-(4-phenylazo-phenylazo)-2-ethylamino-naphthalene (i)

P - 2: (1:2) chromium complex of 4-(2-hydroxy-4-nitro-5-methylsulfonyl-phenylazo)-5-methyl-2-phenyl-3-pyrazolone, sodium salt P - 3: 6-(1-phenylazo-4-naphthyl-azo)-2,3-dihydro-2,2-dimethyl-perimidine (i″)

The felt squares thus impregnated were suspended in a room in which the temperature was kept at 24 ± 2°C and the relative humidity was about 60.

At the end of 12 days, the percentage amounts of DDVP destroyed was measured as described in Experiment C and tabulated as follows:

| P - 0 | P - 1 | P - 2 | P - 3 | P - 00 |
|-------|-------|-------|-------|--------|
| 29.7  | 16.8  | 17.8  | 14.2  | 29.8   |
| ± 1.3 | ± 0.3 | ± 0.8 | ± 0.8 | ± 0.8  |

The results of this experiment show that the presence of the insoluble, red dyestuff of the felt had no stabilizing effect whatever on the DDVP, since the hydrolysis obtained with the red control was as great as the white felt; it is necessary to add one of the diazene compounds contemplated by the invention to reduce said hydrolysis.

EXPERIMENT Q

Squares, 10 × 10 centimeters, cut from "genuine rag", blotting paper manufactured by the French company Papiers Canson, in Vidaloules-Annonai (Ardeche), France, and having a unit weight of 2.45 g, were used; these squares were placed in piles of three each which were clipped together and then dried in an oven at 110°C for 1 hour.

Five different kinds of the above-defined paper, differing only in the color thereof, were used; the five kinds were designated as follows:

Q - 0:   white
    Q - 1:   blue
    Q - 2:   rose
    Q - 3:   yellow
    Q - 4:   red After ascertaining that the dyestuff present in the paper was insoluble in DDVP, the piles of each kind of paper (5 for each kind) were impregnated with 14.2 g of DDVP.

The piles thus treated were suspended in a room in which the temperature was kept at 24 ± 2°C and the relative humidity was about 65.

At the end of 15 days, the percentage amounts of DDVP destroyed were measured as described in Experiment C and tabulated as follows:

| Q - 0 | Q - 1 | Q - 2 | Q - 3 | Q - 4 |
|-------|-------|-------|-------|-------|
| 56.3  | 59.1  | 52.7  | 55.5  | 57.9  |
| ± 1.6 | ± 2.1 | ± 1.7 | ± 1.8 | ± 1.9 |

The results of this experiment confirm the great susceptibility of DDVP to humidity; they also confirm that the stabilizing properties of the diazenes contemplated by the invention are not due to their dyeing power which they have as one of their general properties, but solely due to the action of the diazene chemical grouping, since the coloring of the papers used did not at all reduce the hydrolytic action of the water on DDVP.

EXPERIMENT R

Squares of cardboard such as was used in Experiments C to L, having a unit weight of 8.60 g, of which 0.40 g was water, were used. These squares were arranged in 6 series of 3 units each designated R - 0 to R - 5; the squares R - 0 were impregnated with 17 g of DDVP and the other squares were impregnated with 17 g of a 1 percent solution in DDVP of a dyestuff soluble in that phosphoric acid ester, and not having a diazene group in either of its two forms: azo or hydrazono.

This series of impregnated squares was designated as follows according to the dyestuff used:

```
R - 1:    Acid Violet 5 B (r)
R - 2:    Acid Fuchsine (r')
R - 3:    Rhodamine B (r'')
R - 4:    Eosine (r''')
R - 5:    Saphire Alizarine Acid B (r'''')
``` r. well-known compound (Color Index 44 055), belonging to the class of dyestuffs derived from triphenylmethane, giving a violaceous blue solution with DDVP r'. well-known compound (Color Index 42 685), belonging to the class of dyestuffs derived from triphenylmethane, giving a violet solution with DDVP r''. well-known compound (Color Index 45 170), belonging to the xanthene class of dyestuffs, giving a red solution with DDVP r'''. well-known compound (Color Index 45 380), belonging to the xanthene class of dyestuffs, giving yellow orange solution with DDVP r''''. well-known compound (Farbstofftabellen 1 187), belonging to the anthraquinone class of dyestuffs, giving a blue solution with DDVP.

The squares thus impregnated are suspended in a room in which the temperature was kept at 20 ± 2°C and the relative humidity was about 45.

At the end of 15 days, the percentage amounts of DDVP destroyed were measured as described in Experiment C and tabulated as follows:

| R - 0 | R - 1 | R - 2 | R - 3 | R - 4 | R - 5 |
|-------|-------|-------|-------|-------|-------|
| 31.3 ± 1.0 | 32.4 ± 1.1 | 33.1 ± 0.7 | 31.3 ± 1.4 | 32.7 ± 0.8 | 34.5 ± 0.9 |

The results of this experiment confirm that the stabilizing properties of the diazenes contemplated by the invention are not due to their coloring power, since these stabilizing properties have not been found among other chemical classes of soluble dye-stuffs; the stabilizing properties of the diazenes are therefore due to the presence of the diazene group in their molecule.

EXPERIMENT S

Solutions containing 50 percent by weight of DDVP in various alcohols are prepared; each solution was poured into a series of test tubes; all of the tubes were placed in a water bath the temperature of which was kept at 96°/100°C. Every 2 hours a sample tube was taken from each of the solutions and the acidity was determined potentiometrically, from which then the rate of destruction of DDVP was calculated: the table below shows the rate of destruction after 2, 4, 8, 12 and 20 hours for 4 of the solutions assayed.

| alcohol tested | heating time | | | | |
|---|---|---|---|---|---|
| | 2 | 4 | 8 | 12 | 20 |
| 2-octanol | 9.7% | 16.8% | 17.6% | 38.5% | 55.5% |
| 1-octanol | 3.4% | 32.0% | 47.0% | 58.5% | 71.5% |
| 1-dodecanol | 16.8% | 19.0% | 33.0% | 46.0% | 61.5% |
| linalool | 8.0% | 10.3% | 19.9% | 30.0% | 50.0% |

These results show that the phosphoric acid ester is destroyed as well by tertiary alcohols as by secondary and primary the greatest destruction being with the primary alcohols and the least with the tertiary alcohols.

By further experimentation, moreover, Applicants have found that the degradation products of DDVP and the alcoholic compounds were, respectively, 0-(2,22,2-dichloro-vinyl)-0-methylhydrogenophosphate and methoxy-alkanes, which may be described by following reaction scheme:

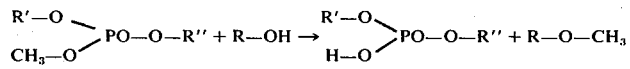

EXPERIMENT T

Seven solutions containing an equimolar mixture of DDVP and 1-butanol were prepared as follows:

| Preparation T - 0 | |
|---|---|
| DDVP, technical: | 74.9% |
| 1-butanol: | 25.1% |

| Preparation T - 1 | |
|---|---|
| Preparation T - 0: | 99 % |
| α-(1-naphthylhydrazono)-[4-(1,2-dihydro-2-oxo-phenylidenehydrazo)-xylyl]-toluene: | 1 % |

| Preparation T - 2 | |
|---|---|
| Preparation T - 0: | 99 % |
| 1-(4-phenylazo-phenylhydrazono)-1,2-dihydro-2-oxo-naphthalene (g): | 1 % |

| Preparation T - 3 | |
|---|---|
| Preparation T - 0: | 99 % |
| 6-(1-phenylazo-4-naphthyl-azo)-2,3-dihydro-2,2-dimethyl-perimidine (i''): | 1 % |

| Preparation T - 4 | |
|---|---|
| Preparation T - 0: | 99 % |
| 1-(4-phenylazo-phenylazo)-2-ethylamino-naphthalene (i): | 1 % |

| Preparation T - 5 | |
|---|---|
| Preparation T - 0: | 99 % |
| (1:2) chromium complex, in equivalent mixture, of the diazo derivative of (2-amino-5-nitro-4-ethylsulfonyl-phenol) 2-(2-carboxy-phenyl)-naphthylamine, sodium salt and the diazo derivative of (2-amino-5-nitro-4-ethylsulfonyl-phenol) 8-hydroxy-quinoline, sodium salt: | 1 % |

| Preparation T - 6 | |
|---|---|
| Preparation T - 0: | 99 % |
| (1:2) chromium complexes, in equivalent mixture, of the following azo compounds: 1-(2-hydroxy-5-nitro-phenylazo)-2-naphthol, sodium salt; 1-(2-hydroxy-4-nitro-phenylazo)-2-naphthol, sodium salt; 1-(2-hydroxy-3-nitro-5-tert-amyl-phenylazo)-2-naphthol, sodium salt: | 1 % |

These preparations were kept for 30 days at 22 ± 2°C in hermetically sealed containers; at the end of that period, the amount of DDVP destroyed was measured potentiometrically.

The amount of acid present in the DDVP was taken into account and this was deducted from the results obtained.

The percentage amounts of the DDVP which decomposed were recorded and are given in the following table:

| T - 0 | T - 1 | T - 2 | T - 3 | T - 4 | T - 5 | T - 6 |
|---|---|---|---|---|---|---|
| 21.0 | 5.3 | 8.0 | 4.9 | 3.1 | 3.2 | 8.7 |

EXPERIMENT U

Seven solutions containing an equimolar mixture of DDVP and 1-octanol were prepared as follows:

Preparation U - 0
DDVP, technical: 62.9%
1-octanol: 37.1%

Preparation U - 1
Preparation U - 0: 99 %
α-(1-naphthylhydrazono)-[4-(1,2-dihydro-2-oxo-phenylidenehydrazo)-xylyl]-toluene: 1 %

Preparation U - 2
Preparation U - 0: 99 %
1-(4-phenylazo-phenylhydrazono)-1,2-dihydro-2-oxo-naphthalene (g): 1 %

Preparation U - 3
Preparation U - 0: 99 %
1-xylylhydrazono-1,2-dihydro-2-oxo-naphthalene (g''): 1 %

Preparation U - 4
Preparation U - 0: 99 %
6-(1-phenylazo-4-naphthyl-azo)-2,3-dihydro-2,2-dimethyl-perimidine (i''): 1 %

Preparation U - 5
Preparation U - 0: 99 %
1-(4-phenylazo-phenylazo)-2-ethylamino-naphthalene (i): 1 %

Preparation U - 6
Preparation U - 0: 99 %
(1:2) chromium complex, in equivalent mixture, of the diazo derivative of (2-amino-5-nitro-4-ethylsulfonyl-phenol) → 2-(2-carboxy-phenyl)-naphthylamine, sodium salt and the diazo derivative of (2-amino-5-nitro-4-ethylsulfonyl-phenol) → 8-hydroxy-quinoline, sodium salt: 1 %

These preparations were kept for 60 days at 22 ± 2°C in hermetically sealed containers; at the end of that period, the amount of DDVP destroyed was measured and the results obtained were tabulated as follows.

| U - 0 | U - 1 | U - 2 | U - 3 | U - 4 | U - 5 | O - 6 |
|---|---|---|---|---|---|---|
| 20.7 | 9.7 | 9.5 | 9.6 | 5.4 | 4.8 | 5.1 |

EXPERIMENT V

Seven solutions containing an equimolar mixture of DDVP and 2-octanol were prepared as follows:

Preparation V - 0
DDVP, technical: 62.9%
2-octanol: 37.1%

Preparation V - 1
Preparation V - 0: 99 %
α-(1-naphthylhydrazono)-[4-(1,2-dihydro-2-oxo-phenylidenehydrazo)-xylyl]-toluene: 1 %

Preparation V - 2
Preparation V - 0: 99 %
1-(4-phenylazo-phenylhydrazono)-1,2-dihydro-2-oxo-naphthalene (g): 1 %

Preparation V - 3
Preparation V - 0: 99 %
1-xylylhydrazono-1,2-dihydro-2-oxo-naphthalene (g''): 1 %

Preparation V - 4
Preparation V - 0: 99 %
6-(1-phenylazo-4-naphthyl-azo)-2,3-dihydro-2,2-dimethyl-perimidine (i''): 1 %

Preparation V - 5
Preparation V - 0: 99 %
1-(4-phenylazo-phenylazo)-2-ethylamino-naphthalene (i): 1 %

Preparation V - 6
Preparation V - 0: 99 %
(1:2) chromium complexes, in equivalent mixture, of the following azo compounds:
1-(2-hydroxy-5-nitro-phenylazo)-2-naphthol, sodium salt;
1-(2-hydroxy-4-nitro-phenylazo)-2-naphthol, sodium salt;
1-(2-hydroxy-3-nitro-5-tert-amyl-phenylazo)-2-naphthol, sodium salt: 1 %

These preparations were treated as described for Experiment U (60 days at 22 ± 2°C) and the results obtained were the following:

| V - 0 | V - 1 | V - 2 | V - 3 | V - 4 | V - 5 | V - 6 |
|---|---|---|---|---|---|---|
| 15.3 | 7.1 | 4.1 | 8.7 | 5.1 | 4.5 | 4.5 |

EXPERIMENT W

Two solutions containing an equimolar mixture of DDVP and tertiary butanol were prepared as follows:

Preparation W - 0
DDVP, technical: 74.9%
tertiary butanol: 25.1%

Preparation W - 1
Preparation W - 0: 99 %
azobenzene (e): 1 %

These preparation were treated as described in Experiment T (30 days at 22 ± 2°C) and the following results were obtained:

| W - 0 | W - 1 |
|---|---|
| 3.8 | 1.9 |

EXPERIMENT X

The same mixtures are prepared as were prepared in Experiment W, being here designated X - 0 and X - 1.

These preparations were kept for 30 days at 40 ± 2°C in hermetically sealed containers; at the end of that period, the percentage amounts of DDVP destroyed were measured and the results obtained were tabulated as follows:

| X - 0 | X - 1 |
|---|---|
| 11.4 | 5.1 |

The results of Experiments T to X clearly show to what extent DDVP is susceptible to the action of an alcoholic compound, even at ambient temperature, when it is not protected.

These experiments also show that this action can be reduced considerably when a diazene is added to the composition containing the phosphoric acid ester and the alcoholic compound.

EXPERIMENT Y

Evaporating devices consisting of cylinders having a diameter of 43 mm and a height of 75 mm; these devices were arranged in two series differing from one another in their formulations:

|  | Y - 1 | Y - 2 |
|---|---|---|
| DDVP | 24.75% | 24.75% |
| modified montmorillonite (x') | 9.00% | 9.00% |
| paraffin 60/62° | 65.75% | 64.75% |
| yellow pigment | 0.50% | 0.50% |
| azobenzene | — | 1.00% | x'. product dried at 80°C so as to contain a maximum of 0.6% of water, comprising a mixture of dimethyl-dihexadecylammonium montmorillonite (70%) and dimethyl-dioctadecylammonium montmorillonite (30%).

The cylinders, obtained by molding a molten mixture were clad by a grill having an optical permeability of about 60 percent and were placed to evaporate in living quarters.

Several tests of their insecticidal effectiveness were carried out on house flies during the period in which the devices were functioning. The results recorded for the cylinders Y-2 were always clearly more favorable than those for the cylinders Y-1. Applicants were, in particular, very surprised to find that an equal rate of evaporation, better results were always observed with the cylinders Y-2; it was particularly surprising that on the 53rd day of functioning, when the cylinders Y-2 were not evaporating more, on an average, than 70 mg per day, these had an effectiveness at least equal and sometimes superior to that of the cylinders Y-1 the operation of which only lasted for 23 days and the average evaporation rate was still 200 mg per day. In order to note a slightly better effectiveness of the cylinders Y-1, it was necessary to reduce the temperature of the room where the experiments were carried out so that the biological activity of the flies was reduced; a difference was noted when the temperature of the cylinders Y-2 was lowered to from 17° to 18°C, the temperature of the room where the cylinders Y-1 were tested being maintained at 22°/23°C.

EXPERIMENT Z

Cardboard of the same quality described in Experiment C was used, but cut to the dimensions 5 × 10 centimeters; these pieces of carcboard were arranged in groups so that two pieces were fastened together in such a manner that they had a double thickness without substantially modifying the total surface.

These double pieces of cardboard were put into four series of three units each, here designated as Z - 0 to Z - 3; the double cardboards Z - 0 were impregnated with 14 g of DDVP and the other double cardboards were impregnated with 14 g of a solution in DDVP of the following compounds in the concentrations given below:

| Z - 1: | azobenzene (e): | 1% |
|---|---|---|
| Z - 2: | 1-(1-phenylazo-4-naphthyl-hydrazono)-1,2-dihydro-2-oxo-naphthalene (m): | 1% |
| Z - 3: | azobenzene (e): | 0.5% |
|  | 1-(1-phenylazo-4-naphthyl-hydrazono)-1,2-dihydro-2-oxo-naphthalene (m): | 0.5% | m. compound obtained from coupling β-naphthol and diazotized 4-phenylazo-α-naphthylamine; this compound is often designated 1-(1-phenylazo-4-naphthyl-azo)-2-naphthol.

The double cardboards thus impregnated were placed in small bags made of Nylon 66 cloth having a thread of 0.14 mm and a mesh of 0.3 mm, manufactured by the French company Tripette and Renaud.

These devices were suspended in a room in which the temperature was kept at 22 ± 2°C and having a relative humidity of about 45.

At the end of 7 days, the percentage amounts of DDVP destroyed were measured as described in Experiment C and tabulated as follows:

| Z - 0 | Z - 1 | Z - 2 | Z - 3 |
|---|---|---|---|
| 28.7 ± 0.6 | 2.1 ± 0.3 | 6.3 ± 0.4 | 1.3 ± 0.1 |

The results of this experiment show the advantage that may result from certain combinations of diazenes; it can be seen that the mixture Z - 3, at a concentration of 1 percent has a superior stabilizing action than either of the compounds Z - 1 or Z - 2 employed at the same concentration, but separately.

EXPERIMENT A A

Squares, 10 × 10 centimeters, cut from a cellulose cardboard, manufactured by the French company Fioroni S.A. under the reference No. 200 are used; at the time of use the cardboard weighed 4,4 g per square.

The cardboard squares were arranged in four series of three each, designated as AA-0 to AA-3; the squares AA-0 were impregnated with 6 grams of 0,0-dimethyl 0-(2,2-dibromovinyl) phosphate and the other squares were impregnated with 6 grams of a 2 percent solution of one of the following compounds in the 0,0-dimethyl 0-(2,2-dibromovinyl) phosphate:

AA-1 : 3-(4-nitro-phenylhydrazono)-2-indolone
AA-2 : 1-(4-phenylazo-phenylazo)-2-ethylamino-naphthalene
AA-3 : (1:2)chromium complex consisting in a mixture of the the following azo compounds:
1-(2-hydroxy-5-nitro-phenylazo)-2-naphthol, sodium salt
1-(2-hydroxy-4-nitro-phenylazo)-2-naphthol, sodium salt
1-(2-hydroxy-3-nitro-5-tert.amyl-phenylazo)-2-naphthol, sodium salt.

The squares thus impregnated were suspended in a room in which the temperature was kept at 22 ± 2°C and in which the relative humidity was about 60%. At the end of 16 days, the amount of phosphoric acid ester destroyed by hydrolysis was measured potentiometrically.

In order to take into account the acidity originally present in the phosphoric acid ester, the acidity which represented 7,4% of the weight of the phosphoric ester, was deducted from the results obtained.

The percentage amounts of 0,0-dimethyl 0-(2,2-dibromovinyl) phosphate decomposed by hydrolysis which were determined are tabulated in the following table;

| AA-0 | AA-1 | AA-2 | AA-3 |
|------|------|------|------|
| 14.8 | 7.0  | 8.6  | 8.6  |

EXPERIMENT AB

Cardboard squares as described in Experiment AA were used, which were arranged in six series, designated AB-0 to AB-6.

The squares AB-0 were impregnated with 6 grams of 0,0-diethyl 0-(2,2-dichlorovinyl) phosphate and the other squares were impregnated with 6 grams of a 2% solution of one of the azo compounds used in experiments AA-1 to AA-3 and also of one of the following compounds in the 0,0-diethyl 0-(2,2-dichlorovinyl) phosphate:

AB-4 : azobenzene
AB-5 : 1-(2-pyridyl-hydrazono)-1,2-dihydro-2-oxo-naphthalene (a)
AB-6 : 1,3,5-triphenyl-1,2,4,5-tetraza-1,3-pentadiene (b)

a. compound which can also be designated by the name of its azo structure which is 1-(2-pyridyl-azo)-2-naphthol.
b. compound which can also be designated by the name of triphenylformazane or by that of phenylformazyle. The acidity originally present represented 2,5% of the weight of the phosphoric acid ester and was deducted from the results obtained.

The impregnated boards were suspended under the same conditions as in experiment AA but for 48 days at the end of which the following amounts of destructed 0,0-diethyl-0-(2,2-dichlorovinyl)-phosphate were potentiometrically measured:

| AB-0 | AB-1 | AB-2 | AB-3 | AB-4 | AB-5 | AB-6 |
|------|------|------|------|------|------|------|
| 7.1  | 2.9  | 3.3  | 0.8  | 2.3  | 2.5  | 1.9  |

EXPERIMENT AC

Cardboard squares as described in Experiment AA were used, which were arranged in four series designated AC-0 to AC-3.

The squares AC-0 were impregnated with 6 grams of 0,0-diethyl 0-(2,2-dibromovinyl) phosphate and the squares AC-1, AC-2 and AC-3 with 6 grams of a 2 percent solution of one of the following azo compound;

AC-1 : 1-(4-phenylazo-phenylazo)-2-ethylaminonaphthalene;
AC-2 : (1:2) chromium complex mixture defined in Experiment AA under denomination AA-3;
AC-3 : 1,2,3-triphenyl-1,2,4,5-tetraza-1,3-pentadiene (b):
b. see remark in Experiment AB.

The acidity originally present in the phosphoric acid ester represented 6,1 percent of this ester and was deducted from the results obtained.

The impregnated boards were suspended under the same conditions as in Experiment AA but for 60 days at the end of which the following amounts of destructed 0,0-diethyl 0-(2,2-dibromovinyl) phosphate were potentiometrically measured:

| AC-0 | AC-1 | AC-2 | AC-3 |
|------|------|------|------|
| 26.4 | 15.4 | 9.4  | 15.4 |

EXPERIMENT AD

Squares, 5 × 10 centimeters as described in Experiment AA were used which at the time of use weighed 895 grams per square meter.

These cardboard squares have been joined together back to back by means of clips. These double squares were arranged in 22 series designed under AD-0 and AD-1/I to III to AD-7/I to III. The double squares of the first serie AD-0 were impregnated with 12,5 g of pure DDVP, whereas those of the remaining series were impregnated with 12,5 grams of a solution of the following stabilizer present in the three different proportions of 0,2, 1 and 3 percent.

AD - 1 Epichlorhydrine
AD - 2 Epoxidized soja bean oil with 6% epoxide oxygen
AD - 3 Azobenzene
AD - 4 4-Diethylaminoazobenzene
AD - 5 1-Phenylazo-2-naphthol
AD - 6 4-Phenylazo-3-methyl-1-phenyl-5-hydroxy-pyrazole
AD - 7 (1:2)chromium complex as described under AA-3 in Experiment AA.

The thus impregnated double squares were suspended in a room in which the temperature was kept at 22 ± 2°C and in which the relative humidity was about 70 percent.

At the end of three weeks, the amount of DDVP destroyed by hydrolysis was measured potentiometrically.

Account was taken of the acidity originally present in the DDVP, which acidity represented 1,45 percent of the weight of the DDVP and was deducted from the obtained results.

The following amounts of destructed DDVP were thus potentiometrically measured:

| Stabilizer | Weight amount of the stabilizer | | |
|------------|------|------|------|
|            | I 0.2% | II 1% | III 3% |
| AD-0 |       | 49.1 |       |
| AD-1 | 49.0  | 48.0 | 37.7  |
| AD-2 | 46.9  | 28.5 | 8.0   |
| AD-3 | 10.2  | 2.3  | 0.5   |
| AD-4 | 1.4   | 1.0  | 0.9   |
| AD-5 | 4.5   | 0.9  | 0.7   |
| AD-6 | 24.6  | 6.7  | 2.9   |
| AD-7 | 1.2   | 0    | 0     |

This experiment shows that diazenes when they are used in evaporator systems according to the invention show better stabilizing properties than epoxide compounds.

EXPERIMENT AE

Squares, 5 × 10 centimeters as described in Experiment AA were used, which at the time of use weighed 895 grams per square meter.

These cardboard squares have been joined together back to back by means of clips.

These double squares were arranged in 31 series designed under AE-0, AE-$1_A$ to AE-$15_A$ and AE-$1_B$ to AE-$15_B$.

The double squares of the series AE-0 were each impregnated with 12.5 grams of DDVP, whereas those of the series AE-$1_A$ to AE-$15_A$ were each impregnated with 12.5 grams of a solution consisting of 0.2 percent by weight of a stabilizer in DDVP, and the series AE-$1_B$ to AE-$15_B$ were impregnated with 12,5 grams of a solution consisting of 2 percent by weight of the same stabilizer compounds in DDVP.

The following stabilizers were tested:

| | |
|---|---|
| AE-1 | azobenzene |
| AE-2 | 4-diethylamino-azobenzene |
| AE-3 | 1-phenylazo-2-naphthol |
| AE-4 | 1-(2-pyridyl-azo)-2-naphthol |
| AE-5 | triphenylformazane |
| AE-6 | (1:2)chromium complex of the following diazenes: 1-(2-hydroxy-5-nitro-phenylazo)-2-naphthol, sodium salt; 1-(2-hydroxy-4-nitro-phenylazo)-2-naphthol, sodium salt; 1-(2-hydroxy-3-nitro-5-ter.amyl-phenylazo)-2-naphthol, sodium salt. |
| AE-7 | acetic anhydride |
| AE-8 | succinic anhydride |
| AE-9 | phthalic anhydride |
| AE-10 | triethylamine |
| AE-11 | piperidine |
| AE-12 | acetic anhydride + triethylamine[a] |
| AE-13 | acetic anhydride + piperidine[a] |
| AE-14 | succinic anhydride + triethylamine[a] |
| AE-15 | phthalic anhydride + piperidine[a]. |

[a]mixture of stoechiometrical quantities.

The thus impregnated double squares were each enclosed in a small bag made of a cloth of polyethylene threads having a diameter of 0.15 mm, said cloth containing 22 threads per centimeter; these devices were then suspended in a room in which the temperature was kept at 25 ± 2°C and in which the relative humidity was of (70 ± 10) percent.

At the end of 4 weeks, the amount of DDVP destroyed by hydrolysis was measured potentiometrically. Account was taken of the acidity originally present in the DDVP, which acidity represented 0.12 percent of the weight of the DDVP and was deducted from the obtained results.

The following table show the amount of destructed DDVP:

| | A 0.5% stabilizer | A 2.0% stabilizer |
|---|---|---|
| AE-0 | 34% | |
| AE-1 | 12.3 | 1.4 |
| AE-2 | 11.4 | 1.0 |
| AE-3 | 1.0 | 0.9 |
| AE-4 | 13.6 | 1.9 |
| AE-5 | 10.4 | 1.4 |
| AE-6 | 1.9 | 0.7 |
| AE-7 | 31.4 | 21.8 |
| AE-8 | 64.1 | 73.1 |
| AE-9 | 71.3 | 69.0 |
| AE-10 | 29.7 | — |
| AE-11 | 31.3 | 48.3 |
| AE-12 | 32.3 | 46.3 |
| AE-13 | 48.8 | 60.5 |
| AE-14 | 43.9 | 64.7 |
| AE-15 | 52.0 | 43.9 |

These results show that the stabilization obtained with a diazene is always much better than that obtained with stabilizers of the prior art.

Non-limitative examples follow which describe certain embodiments of the evaporators according to the instant invention.

EXAMPLE 1 to 43

Compositions which can be used in an evaporator of the type described in Experiment M and comprising DDVP as phosphoric acid ester and a diazene as stabilizer for the ester. These compositions may also contain a solvent for the ester (dioctyl phthalate, dibutyl sebacate, diisooctyl adipate).

(Values are expressed in weight percent).

TABLE I

The diazenes used are designated as follows for convenience of tabulation:
Diazene I: 1-(4-phenylazo-phenylhydrazono)-1,2-dihydro-2-oxo-naphthalene (g)
Diazene II: 1-(2-methoxy-phenylhydrazono)-1,2-dihydro-2-oxo-naphthalene (g')
Diazene III: 1-(4-o-tolylazo-2-methyl-phenylhydrazono)-1,2-dihydro-2-oxo-naphthalene (g''')

| | 1 | 2 | 3 | 4 | 5 | 6 | 7 | 8 | 9 | 10 |
|---|---|---|---|---|---|---|---|---|---|---|
| DDVP | 99 | 98 | 70 | 75 | 71 | 99.7 | 81.6 | 74.6 | 74.7 | 65.5 |
| dioctyl phthalate | — | — | 29.7 | 24.5 | — | — | — | — | 25 | — |
| dibutyl sebacate | — | — | — | — | 28.6 | — | — | — | — | — |
| diisooctyl adipate | — | — | — | — | — | 20 | 18 | 25 | — | 34.4 |
| Diazene I | 1 | — | 0.3 | — | — | 0.3 | — | — | 0.3 | — |
| Diazene II | — | — | — | 0.5 | — | — | — | — | — | 0.1 |
| Diazene III | — | 2 | — | — | 0.4 | — | 0.4 | 0.4 | — | — |

TABLE II

The diazenes used are designated as follows for convenience of tabulation:
Diazene IV: 1-(4-phenylazo-phenylazo)-2-ethylamino-naphthalene (i)
Diazene V: 6-(1-phenylazo-4-naphthyl-azo)-2,3-dihydro-2,2-dimethyl-perimidine (i'')

| | 11 | 12 | 13 | 14 | 15 | 16 | 17 | 18 | 19 | 20 | 21 | 22 |
|---|---|---|---|---|---|---|---|---|---|---|---|---|
| DDVP | 99 | 98 | 70 | 75 | 71 | 79 | 81.5 | 74.5 | 74 | 65 | 78 | 70 |
| dioctyl phtha- | — | — | 29 | 23 | — | — | — | — | 25 | — | — | 24.4 |

TABLE II-continued

The diazenes used are designated as follows for convenience of tabulation:
Diazene IV: 1-(4-phenylazo-phenylazo)-2-ethylamino-naphthalene (i)
Diazene V: 6-(1-phenylazo-4-naphthyl-azo)-2,3-dihydro-2,2-dimethyl-perimidine (i″)

|  | 11 | 12 | 13 | 14 | 15 | 16 | 17 | 18 | 19 | 20 | 21 | 22 |
|---|---|---|---|---|---|---|---|---|---|---|---|---|
| DDVP | 99 | 98 | 70 | 75 | 71 | 79 | 81.5 | 74.5 | 74 | 65 | 78 | 70 |
| dioctyl phthalate | — | — | 29 | 23 | — | — | — | — | 25 | — | — | 24.3 |
| dibutyl sebacate | — | — | — | — | 28 | — | — | — | — | — | 20 | — |
| diisooctyl adipate | — | — | — | — | — | 20 | 18 | 25 | — | 34 | — | 5.5 |
| Diazene IV | 1 | — | 1 | 2 | 1 | 1 | — | — | 1 | 1 | 2 | — |
| Diazene V | — | 2 | — | — | — | — | 0.5 | 0.5 | — | — | — | 0.1 |

TABLE III

The diazenes used are designated as follows for convenience of tabulation:
Metallized diazene VI: chromium complex used in Experiment K (K - 5)
Metallized diazene VII: cobalt complex used in Experiment K (K - 4)
Metallized diazene VIII: chromium complex used in Experiment K (K - 6)
Metallized diazene IX: chromium complex used in Experiment L (L - 15)

|  | 23 | 24 | 25 | 26 | 27 | 28 | 29 | 30 | 31 | 32 | 33 |
|---|---|---|---|---|---|---|---|---|---|---|---|
| DDVP% | 70 | 75 | 71 | 79 | 81 | 74.5 | 74 | 65 | 78 | 70 | 98.5 |
| dioctyl phthalate % | 29.5 | 24 | — | — | — | — | 25 | — | — | 29 | — |
| dibutyl sebacate % | — | — | 28 | — | — | — | — | — | 20 | — | — |
| diisooctyl adipate % | — | — | — | 20 | 18 | 25 | — | 34 | — | — | — |
| Metallized diazene VI | 0.5 | — | — | 1 | — | — | — | — | — | 1 | 1.5 |
| Metallized diazene VII | — | 1 | — | — | — | — | 1 | — | 2 | — | — |
| Metallized diazene VIII | — | — | 1 | — | — | — | — | 1 | — | — | — |
| Metallized diazene IX | — | — | — | — | 1 | 0.5 | — | — | — | — | — |

TABLE IV

The diazenes used are designated as follows for convenience of tabulation:
Diazene X: azobenzene (e)
Diazene XI: azophenetol (f)
Diazene XII: 3-(4-nitro-phenylhydrazono)-2-indolinone (d″)

|  | 34 | 35 | 36 | 37 | 38 | 39 | 40 | 41 | 42 | 43 |
|---|---|---|---|---|---|---|---|---|---|---|
| DDVP | 99 | 99 | 70 | 75 | 71 | 74 | 74 | 65 | 78 | 60.5 |
| dioctyl phthalate | — | — | 29 | 23 | — | — | 25 | — | 20 | — |
| dibutyl sebacate | — | — | — | — | 28 | — | — | — | — | — |
| diisobutyl adipate | — | — | — | — | — | 25 | — | 34 | — | 39.4 |
| Diazene X | 1 | 1 | 1 | — | — | 1 | 1 | — | — | 0.1 |
| Diazene XI | — | — | — | — | 1 | — | — | 1 | — | — |
| Diazene XII | — | — | — | 2 | — | — | — | — | 2 | — |

EXAMPLES 44 to 54

Compositions which can be used in an evaporator of the type described in Experiment M and comprising the component parts given in the Tables I to IV, the present compositions being distinguished by the simultaneous use of two diazenes constituting the stabilizer (values are expressed in weight percent).

TABLE V

|  | 44 | 45 | 46 | 47 | 48 | 49 | 50 | 51 | 52 | 53 | 54 |
|---|---|---|---|---|---|---|---|---|---|---|---|
| DDVP | 70 | 74.2 | 98.8 | 98.8 | 99 | 70 | 70 | 71 | 70 | 70 | 70 |
| dioctyl phthalate | 29.4 | — | — | — | — | 29.4 | 29.4 | — | 29.2 | 29.2 | 29.4 |
| dibutyl sebacate | — | — | — | — | — | — | — | 28 | — | — | — |
| diisooctyl adipate | — | 25 | — | — | — | — | — | — | — | — | — |
| Diazene I | 0.3 | — | 0.8 | — | — | — | — | — | — | 0.3 | — |
| Diazene III | — | 0.4 | — | — | — | — | — | — | — | — | 0.4 |
| Diazene IV | — | — | — | 0.8 | — | — | — | — | — | 0.5 | — |

TABLE V-continued

|  | 44 | 45 | 46 | 47 | 48 | 49 | 50 | 51 | 52 | 53 | 54 |
|---|---|---|---|---|---|---|---|---|---|---|---|
| DDVP | 70 | 74.2 | 98.8 | 98.8 | 99 | 70 | 70 | 71 | 70 | 70 | 70 |
| Diazene V | — | — | — | — | — | — | 0.3 | — | 0.3 | — | 0.2 |
| Metallized diazene VI | — | — | — | — | 0.5 | 0.3 | — | 0.5 | 0.5 | — | — |
| Diazene X | 0.3 | 0.4 | 0.4 | 0.4 | 0.5 | 0.3 | 0.3 | 0.5 | — | — | — |

EXAMPLES 55 to 78

Compositions which can be used in a wick evaporator comprising a reservoir and a wick dipping into the composition and having one part thereof exposed to the air. These compositions comprise DDVP as phosphoric acid ester, a diluent for the ester ("Isopar L"), a co-solvent (3,6,9-trioxa-undecane, 5,8,11-trioxy-pentadecane) and a diazene as stabilizer.

y. co-solvent known as diglycol diethyl ether, sold under the trademark "Diethylcarbitol" by the American company Union Carbide Chemicals Co., New York y'. co-solvent known as diglycol dibutyl ether, sold under the trademark "Dibutylcarbitol" by the company Union Carbide Chemicals Co., cited above y''. commercial product sold under the trademark "Abrac A" by the British company Boake, Doberts & Co., London y'''. distillation fraction between 189° and 205°C of synthetic branched hydrocarbons, containing a mixture of decane, undecane and dodecane, sold by the Esso Standard Oil Company.

TABLE VII

|  | 64 | 65 | 66 | 67 | 68 | 69 | 70 | 71 |
|---|---|---|---|---|---|---|---|---|
| DDVP | 9.2 | 8.5 | 8.5 | 9.2 | 9.2 | 9.8 | 10.6 | 9.2 |
| n-dodecane | — | — | — | — | — | — | — | — |
| "Isopar L" (y''') | 85.28 | 86 | 86.48 | 86.78 | 86.78 | 84.69 | 84.38 | 85.79 |
| 3,6,9-trioxa-undecane (y) | 5.5 | — | — | — | — | 5.5 | 5 | 5 |
| 5,8,11-trioxa-pentadecane (y') | — | 5.48 | 5 | 4 | 4 | — | — | — |
| Diazene I | 0.02 | 0.02 | 0.02 | 0.02 | 0.02 | — | 0.02 | — |
| Diazene II | — | — | — | — | — | 0.01 | — | 0.010 |

TABLE VIII

In this table the chromium complex used in Experiment K (K - 2) is designated Metallized diazene XIII.

|  | 72 | 73 | 74 | 75 | 76 | 77 | 78 |
|---|---|---|---|---|---|---|---|
| DDVP | 9.2 | 8.5 | 8.5 | 9.2 | 9.2 | 10.6 | 9.2 |
| "Isopar L" (y''') | 85.29 | 86 | 86.49 | 86.79 | 86.29 | 84.39 | 85.72 |
| 3,6,9-trioxa-undecane | 5.5 | — | — | — | — | 5 | 5 |
| 5,8,11-trioxa-pentadecane (y') | — | 5.49 | 5 | 4 | 4.5 | — | — |
| Metallized diazene XIII | 0.01 | 0.01 | 0.01 | 0.01 | 0.01 | 0.01 | — |
| Diazene X | — | — | — | — | — | — | 0.08 |

(Values are expressed in weight percent).

TABLE VI

|  | 55 | 56 | 57 | 58 | 59 | 60 | 61 | 62 | 63 |
|---|---|---|---|---|---|---|---|---|---|
| DDVP | 9.2 | 8.5 | 8.5 | 9.2 | 9.2 | 10.6 | 10.6 | 9.7 | 9.7 |
| n-dodecane | — | — | — | — | — | — | — | 85.27 | 85.25 |
| "Isopar L" (y''') | 85.26 | 86 | 86.45 | 86.28 | 86.77 | 84.37 | 84.34 | — | — |
| 3,6,9-trioxy-undecane (y) | 5.5 | — | — | — | — | 5 | 5 | — | — |
| 5,8,11-trioxa-pentadecane (y') | — | 5.45 | 5 | 4 | 4 | — | — | 5 | 5 |
| Diazene IV | 0.04 | 0.05 | 0.05 | — | — | — | 0.06 | — | 0.05 |
| Diazene V | — | — | — | 0.02 | 0.03 | 0.03 | — | 0.03 | — |

EXAMPLES 79–86

Compositions which can be used in a wick evaporator as described in Examples 55 to 58, characterized by having two diazenes constituting the stabilizer (values are expressed in weight percent).

TABLE IX

|  | 79 | 80 | 81 | 82 | 83 | 84 | 85 | 86 |
|---|---|---|---|---|---|---|---|---|
| DDVP | 9.2 | 8.5 | 9.2 | 9.2 | 9.2 | 10.6 | 10.6 | 9.7 |
| "Isopar L" (y''') | 85.18 | 86 | 85.62 | 85.18 | 85.18 | 84.24 | 83.78 | 85.22 |
| 3,6,9-trioxa-undecane (y) | 5.5 | — | 5 | 5.5 | 5.5 | 5 | 5.5 | — |
| 5,8,11-trioxa-pentadecane (y') | — | 5.4 | — | — | — | — | — | 5 |
| Diazene IV | 0.08 | 0.06 | 0.12 | — | — | 0.08 | 0.06 | — |
| Diazene V | — | — | — | 0.04 | — | — | — | 0.04 |
| Diazene I | — | — | — | — | 0.02 | — | — | — |
| Diazene X | 0.04 | 0.04 | 0.06 | 0.08 | 0.1 | 0.08 | 0.06 | 0.04 |

EXAMPLES 87 to 108

Compositions comprising concentrates for an evaporator containing DDVP as phosphoric acid ester, an alcoholic compound selected from acyclic hydroxyl compounds, a solvent for the ester (2-ethyl-butanol, 2-ethanol, 2-butoxyethanol, n-heptanol, 2-ethyl-hexanol, 1-octanol, 2-octanol, 1-dodecenol), a diazene as stabilizer of the ester.

(values are expressed in weight percent).

EXAMPLES 120 to 167

Concentrates for the preparation of scented insecticidal evaporator systems comprising DDVP as phosphoric acid ester, an alcoholic compound selected from acyclic hydroxyl compounds or from alicyclic hydroxyl compounds, an odorant (linalool, terpineol, citronnellol, menthol, octenol, rosewood oil), one or two diazenes as stabilizer.

(Values are expressed in weight percent).

TABLE X

| DDVP | 87 | 88 | 89 | 90 | 91 | 92 | 93 | 94 | 95 | 96 | 97 |
|---|---|---|---|---|---|---|---|---|---|---|---|
|  | 54 | 61 | 55 | 54 | 56 | 72 | 65 | 63 | 67 | 67 | 62 |
| 2-ethyl-butanol | — | — | — | — | — | — | 34 | — | — | — | — |
| 2-ethyl-ethanol | — | — | — | — | — | — | — | 36 | — | — | — |
| 2-butoxy-ethanol | — | — | — | — | — | — | — | — | 32 | — | — |
| n-heptanol | 45 | — | — | — | — | — | — | — | — | — | — |
| 2-ethyl-hexanol | — | — | — | — | — | — | — | — | — | 42 | — |
| 1-octanol | — | 38 | 44.4 | — | — | — | — | — | — | — | — |
| 2-octanol | — | — | — | 45.5 | 43.3 | 27.2 | — | — | — | — | — |
| 1-dodecanol | — | — | — | — | — | — | — | — | — | — | 37 |
| Diazene IV | — | 1 | — | 0.5 | — | 0.8 | — | — | 1 | — | — |
| Diazene V | 1 | — | 0.6 | — | 0.7 | — | 1 | 1 | — | 1 | 1 |

TABLE XI

| DDVP | 98 | 99 | 100 | 101 | 102 | 103 | 104 | 105 | 106 | 107 | 108 |
|---|---|---|---|---|---|---|---|---|---|---|---|
|  | 54 | 61 | 55 | 54 | 56 | 72 | 65 | 63 | 67 | 57 | 62 |
| 2-ethyl-butanol | — | — | — | — | — | — | 34 | — | — | — | — |
| 2-ethyl-ethanol | — | — | — | — | — | — | — | 36 | — | — | — |
| 2-butoxy-ethanol | — | — | — | — | — | — | — | — | 32 | — | — |
| n-heptanol | 45 | — | — | — | — | — | — | — | — | — | — |
| 2-ethyl-hexanol | — | — | — | — | — | — | — | — | — | 42 | — |
| n-octanol | — | 38 | 44.4 | — | — | — | — | — | — | — | — |
| sec-octanol | — | — | — | 45.5 | 43.3 | 27.2 | — | — | — | — | — |
| n-dodecanol | — | — | — | — | — | — | — | — | — | — | 37 |
| Diazene I | 1 | — | 0.6 | 0.5 | — | 0.8 | 1 | — | 1 | 1 | 1 |
| Diazene II | — | 1 | — | — | 0.7 | — | — | 1 | — | — | — |

TABLE XII

| DDVP | 109 | 110 | 111 | 112 | 113 | 114 | 115 | 116 | 117 | 18 | 19 |
|---|---|---|---|---|---|---|---|---|---|---|---|
|  | 54 | 61 | 55 | 54 | 56 | 72 | 65 | 63 | 67 | 57 | 62 |
| 2-ethyl-butanol | — | — | — | — | — | — | 34 | — | — | — | — |
| 2-ethyl-ethanol | — | — | — | — | — | — | — | 36 | — | — | — |
| 2-butoxy-ethanol | — | — | — | — | — | — | — | — | 32 | — | — |
| n-heptanol | 45 | — | — | — | — | — | — | — | — | — | — |
| 2-ethyl-hexanol | — | — | — | — | — | — | — | — | — | 42 | — |
| n-octanol | — | 38 | 44.4 | — | — | — | — | — | — | — | — |
| sec-octanol | — | — | — | 45.5 | 43.3 | 27.2 | — | — | — | — | — |
| n-dodecanol | — | — | — | — | — | — | — | — | — | — | 37 |
| Metallized diazene VII | 1 | — | 0.6 | — | — | — | 1 | — | 1 | — | 1 |
| Metallized diazene VI | — | 1 | — | 0.5 | 0.7 | 0.8 | — | 1 | — | 1 | — |

TABLE XIII

| DDVP | 120<br>92 | 121<br>94 | 122<br>94 | 123<br>95 | 124<br>93 | 125<br>94 | 126<br>94 | 127<br>93 | 128<br>91 | 129<br>94 | 130<br>92 | 131<br>92 |
|---|---|---|---|---|---|---|---|---|---|---|---|---|
| linalool | 7.6 | — | — | — | — | — | — | — | — | — | 3 | 3 |
| terpineol | — | 5.4 | — | — | — | — | — | — | — | — | — | — |
| citronellol | — | — | 5.4 | — | — | — | — | — | — | — | — | — |
| menthol | — | — | — | 4.6 | — | — | — | — | — | .1 | — | — |
| 1-octen-3-ol | — | — | — | — | — | — | — | 2.2 | 2 | — | — | — |
| rosewood oil (z'') | — | — | — | — | 6.6 | — | — | — | 4 | — | — | — |
| spearmint oil (z''') | — | — | — | — | — | 5.6 | — | — | — | 3 | — | — |
| palmorosa oil (z'''') | — | — | — | — | — | — | 5.4 | — | 2.5 | — | — | — |
| lavender oil (z''''') | — | — | — | — | — | — | — | 4 | — | 1.5 | 4.4 | 4.4 |
| Diazene I | 0.4 | — | — | 0.4 | 0.4 | — | 0.6 | 0.8 | 0.5 | — | 0.6 | 0.6 |
| Diazene III | — | 0.6 | 0.6 | — | — | 0.4 | — | — | — | 0.5 | — | — |

(z'') natural essence containing linalool, geraniol and terpineols
(z''') natural essence contaning menthol
(z'''') natural essence containing geraniol and citronellol
(z''''') natural essence containing linalool and geraniol.

TABLE XIV

| DDVP | 132<br>92 | 133<br>94 | 134<br>94 | 135<br>95 | 136<br>93 | 137<br>94 | 138<br>94 | 139<br>93 | 140<br>91 | 141<br>94 | 142<br>92 | 143<br>92 |
|---|---|---|---|---|---|---|---|---|---|---|---|---|
| linalool | 7.6 | — | — | — | — | — | — | — | — | — | 3 | 3 |
| terpineol | — | 5.4 | — | — | — | — | — | — | — | — | — | — |
| citronellol | — | — | 5.4 | — | — | — | — | — | — | — | — | — |
| menthol | — | — | — | 4.6 | — | — | — | — | — | — | — | — |
| 1-Octen-3-ol | — | — | — | — | — | — | — | 2.2 | 2 | — | — | — |
| rosewood oil (z'') | — | — | — | — | 6.6 | — | — | — | —4 | — | — | — |
| spearmint oil (z''') | — | — | — | — | — | 5.6 | — | — | — | 3 | — | — |
| palmarosa oil (z'''') | — | — | — | — | — | — | 5.4 | — | — | — | — | — |
| lavender oil (z''''') | — | — | — | — | — | — | — | 4 | 2.5 | 1.5 | 4.4 | 4.4 |
| Diazene IV | 0.4 | 0.6 | — | — | 0.4 | — | — | 0.8 | 0.5 | — | — | 0.6 |
| Diazene V | — | — | 0.6 | 0.4 | — | 0.4 | 0.6 | — | — | 0.5 | 0.6 | — |

TABLE XV

| DDVP | 144<br>92 | 145<br>94 | 146<br>94 | 147<br>95 | 148<br>93 | 149<br>94 | 150<br>94 | 151<br>93 | 152<br>91 | 153<br>94 | 154<br>92 | 155<br>92 |
|---|---|---|---|---|---|---|---|---|---|---|---|---|
| linalol | 7.6 | — | — | — | — | — | — | — | — | — | 3 | 3 |
| terpineol | — | 5.4 | — | — | — | — | — | — | — | — | — | — |
| citronellol | — | — | 5.4 | — | — | — | — | — | — | — | — | — |
| menthol | — | — | — | 4.6 | — | — | — | — | — | 1 | — | — |
| 1-octen-3-ol | — | — | — | — | — | — | — | 2.2 | 2 | — | — | — |
| rosewood oil (z'') | — | — | — | — | 6.6 | — | — | — | 4 | — | — | — |
| spearmint oil (z''') | — | — | — | — | — | 5.6 | — | — | — | 3 | — | — |
| palmarosa oil (z'''') | — | — | — | — | — | — | 5.4 | — | — | — | — | — |
| lavender oil (z''''') | — | — | — | — | — | — | — | 4 | 2.5 | 1.5 | 4.4 | 4.4 |
| Metallized diazene VIII | — | — | — | 0.4 | 0.4 | — | 0.6 | — | 0.5 | — | 0.6 | — |
| Metallized diazene VI | 0.4 | 0.6 | 0.6 | — | — | 0.4 | — | 0.8 | — | 0.5 | — | 0.6 |

TABLE XVI

| DDVP | 156<br>92 | 157<br>94 | 158<br>95 | 159<br>93 | 160<br>94 | 161<br>93 | 162<br>92 | 163<br>94 | 164<br>91 | 165<br>93 | 166<br>96 | 167<br>93 |
|---|---|---|---|---|---|---|---|---|---|---|---|---|
| linalool | 7.5 | — | — | — | — | 3 | 1 | — | — | 2 | — | — |
| citronellol | — | 5.2 | — | — | — | — | — | 5 | 6.5 | — | — | — |
| menthol | — | — | 4.2 | — | — | — | — | — | — | — | 3 | 4 |
| rosewood oil (z'') | — | — | — | 6.4 | — | — | — | — | 4 | — | — | — |
| palmarosa oil (z'''') | — | — | — | — | 5.3 | — | — | — | — | — | — | — |
| lavender oil (z'' ''') | — | — | — | — | — | 3.2 | 6.4 | — | 1.5 | — | — | 2 |
| Diazene IV | — | — | — | — | — | — | — | 0.4 | — | — | — | — |

TABLE XVI-continued

| DDVP | 156 92 | 157 94 | 158 95 | 159 93 | 160 94 | 161 93 | 162 92 | 163 94 | 164 91 | 165 93 | 166 96 | 167 93 |
|---|---|---|---|---|---|---|---|---|---|---|---|---|
| Diazene V | — | — | — | — | — | — | — | — | 0.5 | 0.5 | — | — |
| Metallized Diazene VI | — | — | — | — | — | — | — | — | 0.5 | — | 0.6 | 0.6 |
| Diazene X | 0.5 | 0.8 | 0.8 | 0.6 | 0.7 | 0.8 | 0.6 | 0.6 | — | 0.5 | 0.4 | 0.4 |

EXAMPLES 168 to 179

Insecticidal compositions for evaporators containing DDVP as active substance, a thermoplastic synthetic resin as solid solvent, a high molecular ester as co-solvent in some cases also serving as plasticizer for the resin, one or more diazenes as stabilizer and in some cases a pigment (values are expressed in weight percent).

TABLE XVII

| DDVP | 168 20 | 169 25 | 170 30 | 171 20 | 172 20 | 173 25 | 174 25 | 175 30 | 176 30 | 177 20.5 | 178 20.5 | 179 25 |
|---|---|---|---|---|---|---|---|---|---|---|---|---|
| polyvinyl chloride | 56 | 62 | 40 | 62 | 60 | 51 | — | — | — | 60 | 60 | — |
| ethylene/vinyl acetate co-polymer (67:33) | — | — | — | — | — | — | 54 | — | — | — | — | 54 |
| vinyl acetate/vinyl chloride co-polymer (10:90) | — | — | — | — | — | — | — | 50 | 54 | — | — | — |
| diisooctyl adipate | 23 | — | — | — | — | — | — | — | — | 9 | — | — |
| tricresyl phosphate | — | 12 | 29 | 12 | — | — | — | 49 | 5 | — | — | — |
| methyl laurate | — | — | — | 5 | 9 | — | — | — | — | — | — | — |
| dioctyl phthalate | — | — | — | — | 10 | 8 | 10 | — | — | — | — | 10 |
| dimethyl succinate | — | — | — | — | — | 15 | — | — | — | 9.5 | 9 | — |
| dimethyl maleate | — | — | — | — | — | — | 10 | — | 10 | — | 10 | 10.5 |
| Diazene X | 0.6 | 0.5 | 1 | 0.5 | 0.5 | 0.7 | 0.6 | 1 | 1 | — | — | — |
| Diazene IV | — | — | — | — | — | — | — | — | — | 0.5 | — | — |
| Metallized diazene VI | — | — | — | — | — | — | — | — | — | — | 0.5 | 0.5 |
| pigment | 0.4 | 0.5 | — | 0.5 | 0.5 | 0.3 | 0.4 | — | — | 0.5 | — | — |

EXAMPLES 180 to 191

Insecticidal composition comprising DDVP as active substance, a paraffin as solid additive, a fossil silica as mineral additive, one or more diazenes as stabilizer and, in several cases, an ethylene/vinyl acetate co-polymer as agent for improving the mechanical properties of the paraffin, a pigment, and/or a modified montmorillonite as dispersing agent for maintaining the homogeneity of the composition before cooling.

TABLE XVIII

| DDVP | 180 23 | 181 25 | 182 25 | 183 25 | 184 25 | 185 24 | 186 24.5 | 187 24.5 | 188 24.5 | 189 24.25 | 190 24.25 | 191 25 |
|---|---|---|---|---|---|---|---|---|---|---|---|---|
| paraffin 60/62° | 60 | 57 | 46 | 46 | 46 | 54 | 54 | 58 | 58.5 | 65.5 | 65.5 | 64.5 |
| ethylene/vinyl acetate copolymer (71:29) | — | — | 12 | 12 | 12 | — | — | — | — | — | — | — |
| diatomaceous earth | 15 | 16 | 15 | 15 | 15 | 15 | 15 | 15 | 15 | — | — | — |
| dioleate amine (x) | — | — | — | — | — | 5 | 5 | — | — | — | — | — |
| modified montmorillonite (x') | — | — | — | — | — | — | — | 1.9 | 1 | 9.0 | 9.0 | 9.0 |
| pigment | 1.5 | 1.5 | 1.5 | 1.5 | 1.5 | 0.5 | 0.7 | — | 1 | 1.0* | — | 0.5* |
| Diazene X | 0.5 | 0.5 | 0.5 | — | 0.5 | 1.5 | 0.8 | — | — | — | — | 1.0 |
| Diazene XI | — | — | — | 0.5 | — | — | — | 0.6 | — | — | 1.0 | — |

*Irgalite Yellow BAW (x) product obtained from reacting, in a molar ratio of 2:1, oleic acid and the following mixture of diamines: hexadecylaminopropylene amine (10%) octadecylaminopropylene amine (5%) octadecenylaminopropylene amine (85%)

(x') mixture of dimethyl dihexadecylammonium montmorillonite (70%) and dimethyl dioctadecylammonium montmorillonite (30%)

It is obvious that the invention is not restricted to the formulations which have been set forth, which only serve to illustrate the many possibilities of applying the invention. In particular, DDVP can be replaced in these formulations by a phosphoric acid ester selected from the following:

(1) 0,0-diethyl 0-(2,2-dichlorovinyl) phosphate;
(2) 0,0-dipropyl 0-(2,2-dichlorovinyl) phosphate;
(3) 0,0-dimethyl 0-(2,2-dibromovinyl) phosphate;
(4) 0,0-diethyl 0-(2,2-dibromovinyl) phosphate;
(5) 0,0-dipropyl 0-(2,2-dibromovinyl) phosphate;

-continued (6) O,O-dimethyl O-(2-bromo-2-chloro-vinyl) phosphate;
(7) O,O-diethyl O-(2-bromo-2-chloro-vinyl) phosphate;
(8) O-ethyl O-methyl O-(2,2-dichlorovinyl) phosphate;
(9) O,O-dimethyl O-(1,2-dibromo-2,2-dichloro-ethyl) phosphate;
(10) O,O-diethyl O-(1,2-dibromo-2,2-dichloro-ethyl)-phosphate;
(11) O,O-dimethyl O-(1-bromo-2,2,2-trichloro-ethyl) phosphate;
(12) O,O-diethyl O-(1-bromo-2,2,2-trichloro-ethyl) phosphate;
(13) O,O-dimethyl O-(1,2,2,2-tetrabromo-ethyl) phosphate;
(14) O,O-diethyl O-(1,2,2,2-tetrabromo-ethyl) phosphate;
(15) O,O-dimethyl O-(1,2,-dibromo-2,2-dichloro-propyl) phosphate;
(16) O,O-diethyl O-(1,2-dibromo-2,2-dichloro-propyl) phosphate;
(17) O,O-dimethyl O-(2,2-dichloro-1-methyl-vinyl)-phosphate;
(18) O,O-diethyl O-(2,2-dichloro-1-methyl-vinyl) phosphate.

We claim:

1. In an evaporator system adapted fo emitting insect killing vapors of an insecticide therefrom in a closed area and comprising a liquid or solid composition therein, which can neither be ingested by the insect nor penetrate into it by contact, which composition contains as the essential constituents:

1. as the sole insecticidal substance, from about 8.5 to 99 percent, calculated on the weight of all the ingredients of at least one volatile phosphoric acid ester (A) of the formula:

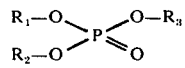  (I)

wherein, $R_1$ and $R_2$ are the same or different and represent alkyl radicals containing 1 to 4 carbon atoms and $R_3$ is a member selected from one of the following groups (i) and (ii):

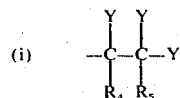

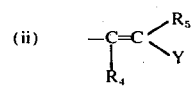

wherein Y is a halogen atom having an atomic weight of at most 80 and
$R_4$ and $R_5$ are identical or different and are selected from the group consisting of a hydrogen atom, an aforesaid halogen atom and a methyl, ethyl or propyl radical, 2. from 0.1 to about 10 percent, based on the weight of (A), of a stabilizing agent (B) for stabilizing the volatile phosphoric acid ester (A) and 3. from 0 to about 90 percent, based on the total weight of the composition, of a solid or liquid diluent
(C) which is a solvent for at least one of components A and B, the improvement wherein the stabilizing agent (B) is such as to prevent the self-protonization reaction of the volatile phosphoric acid ester and is selected from the group consisting of at least one diazene compound of the formula:

$$R - N = N - ZH \quad (IV)$$

and of its corresponding tautomeric hydrazonic formula:

$$R - NH - N = Z$$

wherein ZH is a member selected from the group consisting of

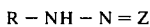

and the group

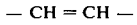

and Z the corresponding tautomeric divalent groups and R, R', R'' and R''' having the following meanings:
R represents a radical of hydroaromatic or of aromatic character comprising one, two or three rings, each having 5 or 6 ring members and when said radical contains two or three rings, the rings are condensed together or bound to each other, directly or via an oxygen atom or an —NH—, —CH$_2$—, or $$- CH = CH -$$

group and when said radical represents three rings, the latter can form a triphenyl methan group; the radical R being selected from the group consisting of
a. carbocyclic radicals of aromatic character having one to three rings and heterocyclic radicals of aromatic character having from one to three rings one of which contains one or two ring hetero atoms chosen from nitrogen, oxygen and sulphur;
b. carbocyclic or heterocyclic radicals with hydroaromatic character having two or three carbocyclic rings each of 5 or 6 ring members and at least two of these rings are condensed together, wherein two or four carbon atoms in one of the rings are saturated and at least one other ring is aromatic;
c. radicals as defined under (a) or (b) substituted by at least one member selected from the group consisting of one or two phenylazo, naphthylazo or arylazoarylazo, in which each of the aryl radicals is phenyl or naphthyl, or 4-pyrazolyl-azo groups; and
d. a radical as defined under (a), (b), or (c) with at least one of its rings bearing one to four substituents selected from fluorine, chlorine, bromine, iodine, keto oxygen, hydroxy, carboxy, alkyl having from one to six carbon atoms, alkylene having from two or five carbon atoms, cycloalkyl having five or six carbon atoms, amino, alkanoylamino having up to five carbon atoms, mono-benzoylamino, alkoxy having from one to five carbon atoms, benzyloxy, nitro, sulpho, cyano, carbamoyl, benzoyl, amino substituted by one or two groups selected from the group consisting of alkyl groups having one to four carbon atoms, phenyl groups and benzyl groups, alkoxycarbonyl having from two to six carbon atoms, alkylsulphonyl having from one to five carbon atoms, sulphamoyl, the nitrogen atom of which is unsubstituted or substituted by one or two hydrocarbon radicals having a total of one to eight carbon atoms, alkanoyloxy having at most eighteen carbon atoms, and alkenoyloxy having at most eighteen carbon atoms, alkanoyl having up to five carbon atoms, and dialkylamino-alkyl having a total of from three to nine carbon atoms; and R' is a member selected from the group consisting of benzyl, alkyl of from one to seventeen carbon atoms, alkenyl of two to eight carbon atoms and a radical R as defined under any one of (a) to (d) as defined above and R'' is a member selected from the group consisting of a radical R' as defined above, an unsubstituted phenylazo or naphthylazo group and a phenylazo or naphthylazo group substituted by methyl or ethyl; or R' and R' taken together represent a divalent hydrocarbon radical having a total of four to fourteen carbon atoms which is a straight or branched chain radical or a chain radical containing an aryl ring condensed to the chain, any substituent of said hydrocarbon radical being selected from the substituents defined under (d), and groups of the formula =NX, in which X represents hydrogen, alkyl having from one to five carbon atoms or phenyl, and the group of formula:

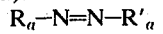

represents a radical R as defined under (a) to (d) above other than a group

as defined above wherein R' and R'' are taken together, or (ii) a salt of a compound as defined under (i) above being at least one group capable of salt formation or, (iii) a metal complex of a compound or salt as defined under (i) or (ii) bearing one or two groups capable of metal complex formation selected from hydroxy, carboxy, amino, mono ($C_1$–$C_4$ alkyl) amino, phenylamino, phenylsulphonamino and ($C_1$–$C_4$ alkyl) sulphonamido groups, said diazene being soluble in said composition.

2. An evaporator system according to claim 1, wherein the diazenes are selected from the group consisting of (a). mono-azo compounds defined by the formula:
$R_a$—N=N—$R'_a$
wherein $R_a$ and $R'_a$ are the same or different and each represents phenyl, naphthyl, pyridyl, quinolyl or diphenyl;

b. mono-azo compounds defined by the formula:

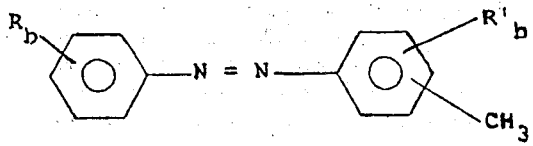

wherein $R_b$ represents hydrogen or one or two methyl radicals, $R'_b$ represents hydrogen or a methyl radical;

c. mono-azo compounds defined by the following formula

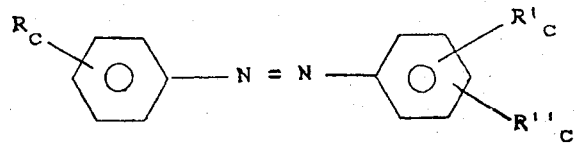

wherein $R_c$ represents hydrogen or one or two halogens, $R'_c$ represents halogen, and $R''_c$ represents hydrogen or halogen being chlorine, bromine, fluorine or iodine;

d. mono-azo compounds defined by the following formula:

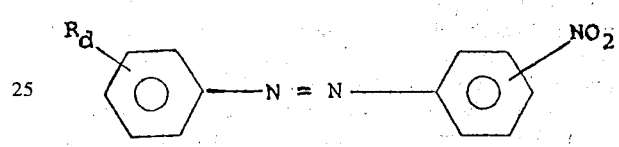

wherein $R_d$ represents hydrogen or a nitro group;

e. mono-azo amino compounds defined by the following formula or by the tautomeric formula of the corresponding iminohydrazone compounds:

$R_e$ — N = N — $R'_e$ wherein $R_e$ represents a phenyl or naphthyl radical substituted by one or two amino groups which are unsubstituted or substituted by an acetyl or benzoyl radical, by one or two phenyl or benzyl radicals or by alkyl having 1 to 4 carbon atoms, the radical $R_e$ being unsubstituted or further substituted by one to three substituents selected from the group consisting of alkyl radicals having 1 to 5 carbon atoms, chlorine, nitro, alkoxy groups having 1 to 3 carbon atoms, alkylsulfonyl groups having 1 to 4 carbon atoms and sulfamoyl groups, the latter being unsubstituted or N-substituted by one or two alkyl radicals having 1 to 4 carbon atoms; $R'_e$ represents a phenyl, naphthyl or pyrazolyl radical, unsubstituted or substituted by one to three substituents selected from the group consisting of methoxy, ethoxy, propoxy groups, methyl, ethyl, phenyl and cyclohexyl radicals and chlorine, nitro and amino groups, the latter being unsubstituted or substituted by one or two phenyl, benzyl or alkyl radicals having 1 to 4 carbon atoms;

f. mono-azo compounds defined by the following formula or by the tautomeric formula of the corresponding hydrazonoquinone compounds:

$R_f$ — N = N — $R'_f$ wherein $R_f$ represents a phenyl, naphthyl or quinolyl radical having one or two hydroxy groups and is unsubstituted or substituted by one to three further substituents chosen from chlorine, alkyl radicals containing 1 to 5 carbon atoms, the cyclohexyl radical, and carbamoyl, carboxy and nitro groups;

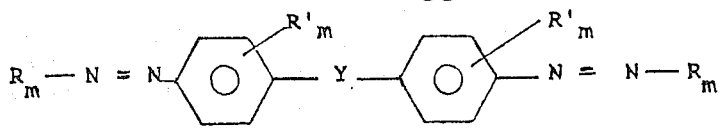

R'_f represents a phenyl, naphthyl or pyridyl radical unsubstituted or substituted by one to four substituents selected from the group consisting of chlorine, the cyclohexyl radical, the methyl radical hydroxy, nitro, methoxy, benzyloxy, dimethylamino and dimethylaminomethyl groups;

g. mono-azo compounds defined by the following formula

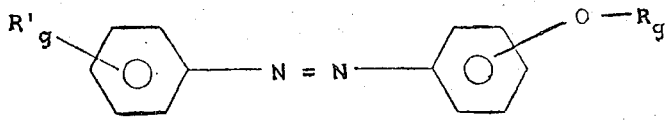

wherein $R_g$ represents an alkyl radical containing 1 to 4 carbon atoms or an alkanoyl radical containing 2 to 18 carbon atoms, $R'_g$ represents hydrogen or an alkoxy group containing 1 to 4 carbon atoms;

(h) phenylhydrazone compounds defined by the formula

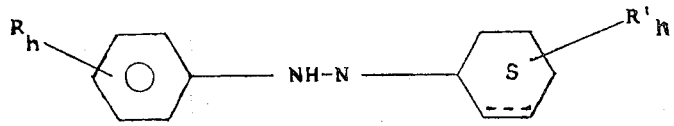

wherein $R_h$ represents hydrogen or one or two substituents chosen from chlorine and nitro $R'_h$ represents hydrogen or one to three alkyl radicals having 1 to 4 carbon atoms, the dotted line represents an optical second bond;

j. phenylhydrazone compounds defined by the following formula or by the tautomeric formula of the corresponding hydroxyazo compounds:

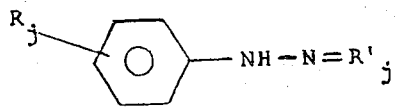

wherein $R_j$ represents one to three substituents selected from the group consisting of alkyl radicals having 1 to 5 carbon atoms, chlorine, nitro, hydroxy, carboxy, sulfo and methylsulfonyl groups; $R'_j$ represents a 2-indolinon-3-ylidene or a 3,4-dihydro-3-pyrazolon-4-ylidene radical, unsubstituted or substituted by a methyl or phenyl, or by both a methyl and phenyl, a chlorophenyl or a sulfophenyl radical;

k. symmetric disazo compounds defined by the following formula or by the tautomeric formula of the corresponding hydrazonoquinone or iminohydrazene compounds when the disazo compound is described as having hydroxy or amino groups:

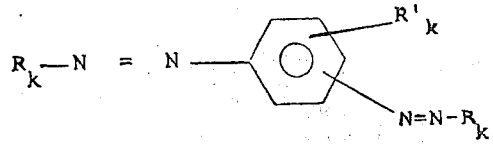

wherein $R_k$ represents a phenyl radical unsubstituted or substituted by an amino group or one or two hydroxy or methyl or by both a hydroxy and methyl; $R'_k$ represents hydrogen or methyl;

m. symmetric disazo compounds defined by the following formula or by the tautomeric formula of the corresponding hydrazonoquinone or iminohydrazone compounds:

wherein Y represents a direct bond or an oxygen atom or a —CH=CH—, -CH$_2$— or —CHR''$_m$— group in which R''$_m$ is a phenyl or chlorophenyl radical; $R_m$ represents a phenyl, naphthyl or 5-pyrazolon-4-yl radical, which radical is unsubstituted or substituted by one or two substituents chosen from methyl, phenyl, hydroxy, amino, sulfo and carboxy groups; $R'_m$ represents one or two hydrogen atoms or one or two methyl radicals;

n. symmetric disazo compounds defined by the following formula or by the tautomeric formula of the corresponding hydrazonoquinone or iminohydrazone compounds when the disazo compound is described as having at least one hydroxy or amino group;

wherein $R_n$ represents a phenyl, diphenyl or naphthyl radical unsubstituted or substituted by one or two substituents selected from the group consisting of a methyl radical, hydroxy, carboxy and sulfo groups; $R'_n$ represents a divalent, phenylene or naphthylene radical, unsubstituted or substituted by one to three substituents selected from the group consisting of a methyl radical, amino, hydroxy, nitro and sulfo groups; $R''_n$ represents a phenyl, naphthyl, tetrahydronaphthyl or dihydro-perimidinyl radical, unsubstituted or substituted by one to four substituents selected from the group consisting of a methyl radical, hydroxy, sulfo, carboxy and amino groups, the latter being unsubstituted or substituted by a methyl or ethyl radical and a sulfamoyl group unsubstituted or N-substituted by one or two alkyl radicals having 1 to 4 carbon atoms;

o. poly-azo compounds defined by the following formula or by the tautomeric formula of the corresponding hydrazonoquinone or iminohydrazone compounds when the compound is described as having at least one hydroxy or amino group:

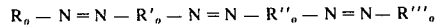

wherein $R_o$ represents a phenyl or naphthyl radical, unsubstituted or substituted by one to four substituents selected from the group consisting of hydroxy, carboxy, amino, sulfo and phenylazo or naphthylazo groups, the latter two groups being unsubstituted or substituted by one or two substituents selected from the group consisting of hydroxy, amino, sulfo and nitro groups; $R'_o$ represents a divalent, non-substituted phenylene or diphenylene radical; $R''_o$ represents a divalent phenylene or naphthylene radical, which is unsubstituted or substituted by one to four substituents selected from the group consisting of amino, hydroxy and sulfo groups; $R'''_o$ represents a phenyl or naphthyl radical unsubstituted or substituted by one or two substituents selected from the group consisting of amino, hydroxy and sulfo groups; (p) formazyl compounds defined by the formula

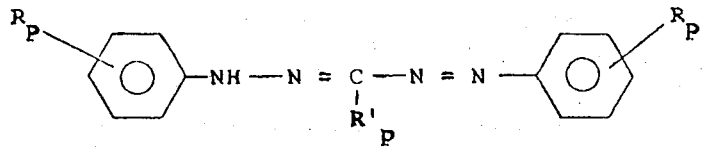

wherein $R_p$ represents hydrogen or a methyl or ethyl radical; $R'_p$ represents a phenyl or benzyl radical or an alkyl radical having 1 to 3 carbon atoms or an alkenyl radical having 2 to 4 carbon atoms;
 g. salts formed from organic or mineral acids and a diazene as defined above having at least one basic function selected from the group consisting of amino, mono ($C_1 - C_4$ alkyl) amino, phenylamino, phenylsulfamido and ($C_1 - C_4$ alkyl) sulfamido;
 r. salts formed from a metal or nitrogen base and a diazene as defined above having at least one acid function selected from the group consisting of hydroxy, carboxy and sulfonic groups;

3. An evaporator system according to claim 1 comprising a diluent (C) which is selected from:
 a. aliphatic or cycloaliphatic hydrocarbons having a vapor pressure at 20°C up to 30 Torr;
 b. aromatic hydrocarbons corresponding to the following formula:

in which $R_q$ is hydrogen or alkyl of 1–5 carbon atoms and $R'_q$ represents one to three alkyl groups containing 1–4 carbon atoms located at any position on the benzene nucleus. $R_q$ and /$R'_q$ can also represent together a saturated divalent hydrocarbon group containing 1–4 carbon atoms;
 c. halogenated aliphatic hydrocarbons containing 6–14 carbon atoms in straight or branched chain and one atom of chlorine or bromine, or 2–8 carbon atoms in straight or branched chain and 2–6 chlorine atoms or 2–4 bromine atoms, one to three of these latter being replaceable with 1–3 chlorine atoms;
 d. halogenated aromatic hydrocarbons corresponding to the following formula

in which $R_r$ is hydrogen or alkyl of 1–5 carbon atoms and $R''_r$ represents at least one member selected from the group consisting of one to three atoms of chlorine and bromine;

e. monoethers correspondng to the following formula:

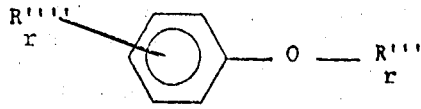

in which $R'''_4$ is alkyl of 1–6 carbon atoms and $R'''_r$ is a halogen selected from the group consisting of chlorine and
 f. diethers of the formula

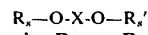

wherein $R_s$ or $R'_s$ are the same or different and are alkyl of 1 to 6 carbons, X represents a divalent hydrocarbon group containing 1 to 6 carbons in straight or branched chain or is benzene;
 g. triethers of the formula

wherein $R''_t$ and $R'''_t$ are the same or different and are alkyl of 1 to 5 carbons, $Y_1$ and $Y'$ are the same or different and are divalent hydrocarbon groups containing 1 to 3 carbons in straight or branched chain;
 h. triethers of the formula

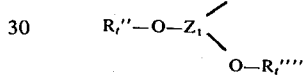

wherein $R''_t$, $R'''_t$ and $R''''_t$ are the same or different and are alkyl of 1 to 5 carbons, $Z_1$, represents a trivalent hydrocarbon group containing 1 to 3 carbons in branched or straight chain or is benzene;
 i. tetraethers of the formula

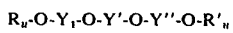

in which $R_u$ and $R'_u$ are the same or different and are an alkyl of 1 to 4 carbons, $Y_1$, $Y'$ and $Y''$ are the same or different and are divalent hydrocarbon groups of 1 to 3 carbons in straight or branched chain;
 j. pentaethers of the formula

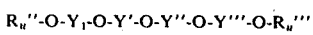

wherein $R''_u$ and $R'''_u$ are the same or different and are alkyl of 1 to 3 carbons, $Y_1$, $Y'$, $Y''$ and $Y'''$ are the same or different and are divalent hydrocarbon groups of 1 to 3 carbons in straight or branched chain, and
 k. heterocyclic compounds of the formula

wherein X is O or S and $A_o$ is the divalent group butadiene-1,3-diyl or 1,4-butanediyl or 3-thia-1,5-pentanediyl or 2-oxa-1,5-pentanediyl or 3-oxa-1,5-pentanediyl, which divalent group is either unsubstituted or substituted by phenyl or by 1 to 4 alkyl substituents of 1 to 4 carbons or by both phenyl and the aforementioned alkyl.

4. An evaporator system according to claim 1 comprising a diluent (C) which is selected from:

—1° Primary, secondary or tertiary, saturated or non-saturated, aliphatic hydroxylated compounds corresponding to the following general formula:

wherein $X_a$ represents a member selected from the group consisting of hydrogen or chlorine, alkylthio, alkoxy containing 1 to 10 carbon atoms and an alkoxyalkoxy group containing 2 to 6 carbon atoms; $A_1$ represents a divalent, straight or branched-chain hydrocarbon group containing 2 to 6 carbon atoms which number may be up to 20 carbon atoms when $X_a$ represents a hydrogen atom;

—2° alicyclic hydroxylated compounds corresponding to the following general formula:

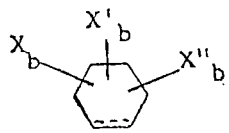

wherein $X_b$ represents a hydrogen atom or one to four alkyl radicals containing 1 to 5 carbon atoms; $X'_b$ represents a hydrogen atom or an alkenyl radical containing 2 to 4 carbon atoms; $X''_b$ represents a hydroxy group or a hydroxyalkyl group containing 1 to 5 carbon atoms; the dotted line represents an optional second bond;

—3° araliphatic alcohols being aralkanols or aralkenols corresponding to the following general formula:

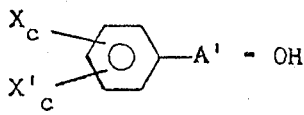

wherein $A'$ represents a saturated or ethylenically unsaturated, straight or branched-chain aliphatic hydrocarbon group containing up to 5 carbon atoms; $X_c$ represents a hydrogen atom or 1 to 5 halogen atoms selected from the group consisting of chlorine or bromine; $X'_c$ represents a hydrogen atom or 1 to 3 alkyl radicals containing 1 to 6 carbon atoms, the total number of $X_c + X'_c$ not exceeding five;

—4° polyols corresponding to the following general formula:

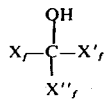

wherein $X_f$ represents either an alkyl radical having 1 to 6 carbon atoms and substituted by 1 to 5 hydroxy groups, said radical being optionally further substituted by a phenyl, chlorophenyl a nitrophenyl radical, or an alkanolylamino group having 2 to 6 carbon atoms and which may be substituted by 1 to 3 chlorine atoms; $X'_f$ represents a hydrogen atom, an alkyl radical having 1 to 6 carbon atoms or a phenyl radical which may be optionally substituted by at least one member selected from the group consisting of 1 to 3 chlorine atoms and by a nitro groups; $X''_f$ represents a hydrogen atom or an alkyl radical having 1 to 4 carbon atoms and optionally substituted by 1 to 3 chlorine atoms;

—5° esters of the above polyols having at least one free hydroxy group and formed from saturated or ethylenically unsaturated aliphatic acids having 2 to 20 carbon atoms;

—6° oxirane condensation, alkylene oxide, products corresponding to the general formula:

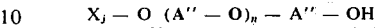

wherein $A''$ represents a straight or branched-chain, saturated aliphatic hydrocarbon group having 1 to 4 carbon atoms; n represents a whole number from 1 to 150; $X_j$ represents a hydrogen atom, an alkyl radical containing 1 to 6 carbon atoms, or an alkanoyl or alkenoyl group having 2 to 20 carbon atoms.

5. An evaporator system according to claim 4 comprising a diluent (C) which is selected from:

1a. aliphatic alcohols of the formula:

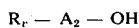

wherein $R_v$ represents hydrogen, an alkoxy of 1–6 carbon atoms or alkoxyalkoxy of 2–6 carbon atoms, $A_2$ is a straight or branched chain hydrocarbon group of 1–6 carbon atoms, this number being up to 14 carbon atoms when $R_v$ is hydrogen;

2a. alicyclic alcohols of the formula:

in which $R_w$ is hydrogen or one or four alkyl groups of 1–5 carbon atoms; and 3a. aralkanols of the formula:

wherein $R'_w$ is hydroxyalkyl of 1–5 carbon atoms, and $R''_w$ represents at least one member selected from the group consisting of and one to two alkyl groups of 1–4 carbon atoms.

6. An evaporator system according to claim 1, wherein the insecticidal active substance (A) is a member selected from the group consisting of O,O-dimethyl O-(2,2-dichlorovinyl) phosphate, O,O-dimethyl O-(2,2-dibromovinyl) phosphate, O,O-diethyl O-(2,2-dichlorovinyl) phosphate and O,O-diethy-O(2,2-dibromovinyl) phosphate.

7. An evaporator system according to claim 6, wherein the insecticidal active substance (A) is O,O-dimethyl O-(2,2-dichlorovinyl) phosphate.

8. An evaporator system according to claim 1, comprising about 3 to 25 percent by weight, based on the total weight of the composition, of the insecticidal active substance (A).

9. An evaporator system according to claim 1, comprising at least two diazene compounds.

10. An evaporator system according to claim 1, wherein the stabilizing agent is present in an amount of from about 0.3 to 5.0 percent, based on the weight of the volatile phosphoric acid ester.

* * * * *